(12) United States Patent
Batram et al.

(10) Patent No.: US 8,709,745 B2
(45) Date of Patent: Apr. 29, 2014

(54) METHODS FOR ISOLATING LIGANDS OF THE HUMAN BITTER TASTE RECEPTOR TAS2R49

(75) Inventors: Claudia Batram, Dissen-Striesow (DE); Wolfgang Meyerhof, Norderstedt (DE)

(73) Assignee: Deutsches Institut für Ernährungsforschung Potsdam-Rehbrücke, Nuthetal (DE)

( * ) Notice: Subject to any disclaimer, the term of this patent is extended or adjusted under 35 U.S.C. 154(b) by 0 days.

(21) Appl. No.: 13/384,956

(22) PCT Filed: Jul. 28, 2010

(86) PCT No.: PCT/EP2010/004623
§ 371 (c)(1),
(2), (4) Date: Apr. 27, 2012

(87) PCT Pub. No.: WO2011/012298
PCT Pub. Date: Feb. 3, 2011

(65) Prior Publication Data
US 2012/0208845 A1   Aug. 16, 2012

Related U.S. Application Data

(60) Provisional application No. 61/271,890, filed on Jul. 28, 2009.

(51) Int. Cl.
*C12Q 1/02* (2006.01)
*G01N 33/53* (2006.01)
*G01N 33/567* (2006.01)
*C07D 311/00* (2006.01)

(52) U.S. Cl.
USPC .............. 435/29; 435/7.2; 435/7.21; 549/400

(58) Field of Classification Search
None
See application file for complete search history.

(56) References Cited

FOREIGN PATENT DOCUMENTS

| WO | WO 2004/029087 | 4/2004 |
| WO | WO 2005/007891 | 1/2005 |
| WO | WO 2006/053771 | 5/2006 |

OTHER PUBLICATIONS

Bufe et al., "The human TAS2R16 receptor mediates bitter taste in response to β-glucopyranosides", *Nature Genetics*, 2002, vol. 32, No. 3, pp. 397-401.
Meyerhof et al., "The Molecular Receptive Ranges of Human TAS2R Bitter Taste Receptors", *Chemical Senses*, 2010, vol. 35, No. 2, pp. 157-170.

*Primary Examiner* — Robert Landsman
(74) *Attorney, Agent, or Firm* — Saliwanchik, Lloyd & Eisenschenk

(57) ABSTRACT

The present invention relates to agonists and antagonists of the human bitter-taste receptor hTAS2R49. The invention also relates to methods for identifying further molecules that suppress or enhance hTAS2R49-mediated bitter taste transduction or bitter taste response and uses thereof.

19 Claims, 7 Drawing Sheets

Fig. 5A

| compound | CAS number | structure | test concentration (mM) |
|---|---|---|---|
| acetaminophen | 103-90-2 | 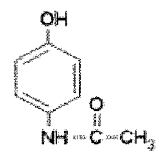 | 3 |
| aloin | 1415-73-2 | 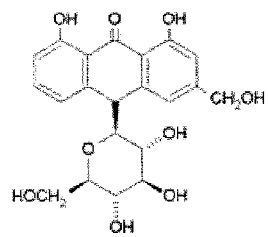 | 0.01 |
| alverine | 5560-59-8 | 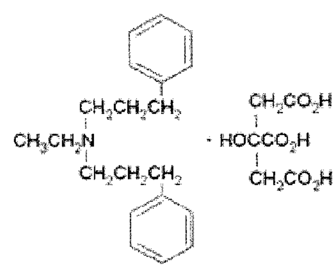 | 0.01 |
| 9-aminoacridine hydrochlorid hydrat | 52417-22-8 | 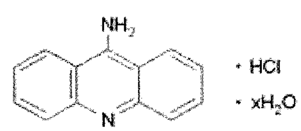 | 0.001 |
| amitriptyline hydrochlorid | 549-18-8 | 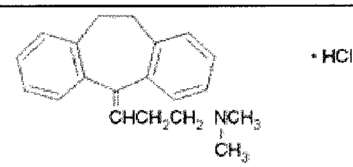 | 0.003 |
| amoxicillin | 26787-78-0 | 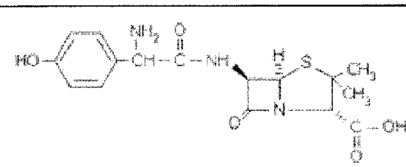 | 5.0 |

| compound | CAS number | structure | test concentration (mM) |
|---|---|---|---|
| D-amygdalin | 29883-15-6 | 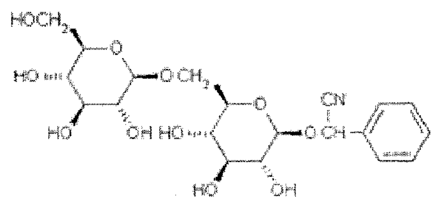 | 30.0 |
| berberine chloride | 633-65-8 | 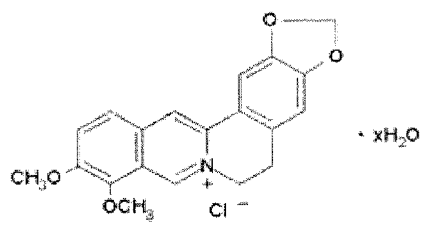 | 0.01 |
| benzamide | 55-21-0 | 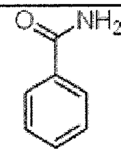 | 0.1 |
| brucine | 357-57-3 | 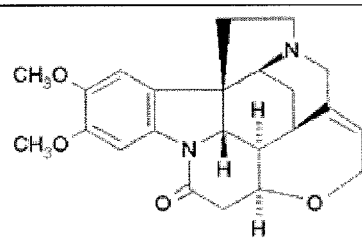 | 0.1 |
| (±)-camphor | 76-22-2 | 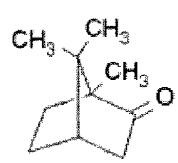 | 1.0 |
| chloramphenicol | 56-75-7 | 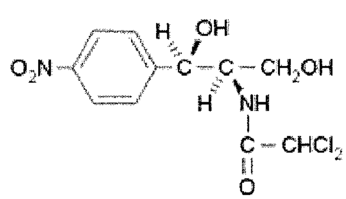 | 1.0 |

Fig. 5C

| compound | CAS number | structure | test concentration (mM) |
|---|---|---|---|
| chlorogenic acid | 327-97-9 | 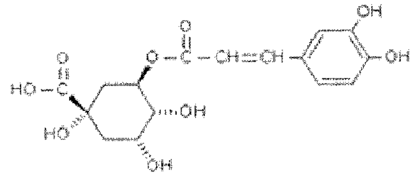 | 1.0 |
| 4,4'-diaminodiphenyl sulfone | 80-08-0 | 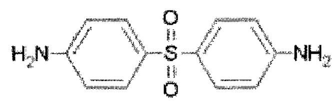 | 0.1 |
| dicyclomine | 67-92-5 | 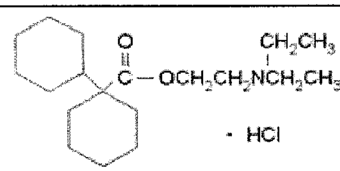 | 0.01 |
| famotidine | 76824-35-6 | 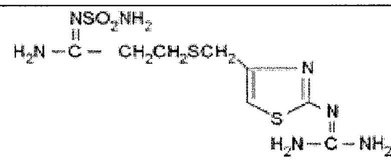 | 0.3 |
| helicin | 618-65-5 | 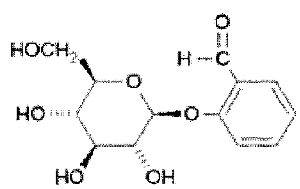 | 10.0 |
| methimazole | 60-56-0 | 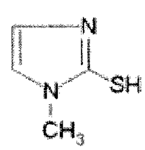 | 10.0 |
| picrotoxinin | 17617-45-7 | 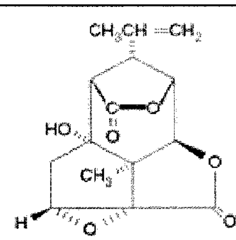 | 1.0 |

…

METHODS FOR ISOLATING LIGANDS OF THE HUMAN BITTER TASTE RECEPTOR TAS2R49

CROSS REFERENCE TO A RELATED APPLICATION

This application is a National Stage Application of International Application No. PCT/EP2010/004623, filed Jul. 28, 2010; which claims the benefit of U.S. Provisional Application Ser. No. 61/271,890, filed Jul. 28, 2009; which are incorporated herein by reference in their entirety.

The present invention relates to agonists and antagonists of the human bitter-taste receptor hTAS2R49. The invention also relates to methods for identifying further molecules that suppress or enhance hTAS2R49-mediated bitter taste transduction or bitter taste response and uses thereof.

BACKGROUND OF THE INVENTION

Investigators have recently turned their attention to understanding the biological mechanisms of taste, and in particular bitter taste. For a review of the literature see, for example, Caicedo A. and Roper S D. (2001) Science 291: 1557-1560; Dulac C. (2000) Cell 100: 607-610; Kinnamon S. C. (2000) Neuron 25: 507-510; Lindemann B. (2001) Nature 413: 219-225.; and Margolskee R F. (2001) J. Biol. Chem. 277: 1-4.

Bitter taste is aversive, and as such provides humans with a mechanism of protection against poisonous substances, which are generally bitter-tasting compounds. More subtly, bitter-tastants also affect the palatability of food, beverages, thereby influencing human nutritional habits as is more fully discussed by Drewnowski in "The Science and Complexity of Bitter Taste", (2001) Nutr. Rev. 59: 163-169. They also affect the palatability of other ingestibles such as orally administered pharmaceuticals and nutraceuticals. Understanding the mechanism of bitter taste transduction has implications for the food and pharmaceutical industries. If the bitter taste transduction pathway can be manipulated, it may be possible to suppress or eliminate bitter taste to render foods more palatable and increase patient compliance with oral pharmaceutics.

Taste transduction involves the interaction of molecules, i.e. tastants with taste receptor-expressing cells which reside in the taste buds located in the papillae of the tongue. Taste buds relay information to the brain on the nutrient content of food and the presence of poisons. Recent advances in biochemical and physiological studies have enabled researchers to conclude that bitter taste transduction is mediated by so-called G-protein coupled receptors (GPCRs). GPCRs are 7 transmembrane domain cell surface proteins that amplify signals generated at a cell surface when the receptor interacts with a ligand (a tastant) whereupon they activate heterotrimeric G-proteins. The G-proteins are protein complexes that are composed of alpha and beta-gamma sub- units. They are usually referred to by their alpha subunits and classified generally into 4 groups: G alpha s, i, q and 12. The G alpha q type couple with GPCRs to activate phospholipase C which leads to an increase in cellular $Ca^{2+}$. There are many Gq-type G-proteins that are promiscuous and can couple to GPCRs, including taste receptors, and these so-called "promiscuous" G-proteins are well known in the art. These G-proteins dissociate into alpha and beta-gamma subunits upon activation, resulting in a complex cascade of cellular events that result in the cell producing second messengers, such as calcium ions, that enable the cells to send a signal to the brain indicating a bitter response.

There is also anatomical evidence that GPCRs mediate bitter taste transduction: clusters of these receptors are found in mammalian taste cells containing gustducin. Gustducin is a G-protein subunit that is implicated in the perception of bitter taste in mammals see, for example, Chandrashekar, J. et al. (2000) Cell 100: 703-711; Matsunami H. et al. (2000) Nature 404: 601- 604; or Adler E. et al. (2000) Cell 100: 693-702. cDNAs encoding such GPCRs have been identified, isolated, and used as templates to compare with DNA libraries using in-silico data-mining techniques to identify other related receptors. In this manner it has been possible to identify a family of related receptors, the so-called T2R or TAS2R family of receptors, which have been putatively assigned as bitter taste receptors.

Humans are able to detect with a limited genetic repertoire of about 30 receptor genes thousands of different bitter compounds. Since their discovery in the year 2000 (Adler E. et al. (2000) supra; Chandrashekar J. et al. (2000) supra; Matsunami H. et al (2000) supra) only few mammalian TAS2Rs have been deorphanised, i.e. ligands, in particular agonists have been identified. The murine mTAS2R5 (Chandrashekar J. et al (2000) supra) and the rat rTAS2R9 (Bufe B. et al. (2002) Nature Genetics 32:397-401) respond to the toxic bitter substance cycloheximide, the mouse mTAS2R8 and the human hTAS2R4 respond to high doses of denatonium and, to a lesser extent, to 6-n-propyl-2-thiouracil (Chandrashekar J. et al. (2000) supra), the human hTAS2R10 and hTAS2R16 respond selectively to strychnine and bitter glucopyranosides, respectively (Bufe B. et al (2002) supra). Although for some TAS2Rs a limited promiscuity (mTAS2R8, hTAS2R4) or specificity for a group of chemically related compounds (hTAS2R16) was reported, the relative selectivity of ligand recognition by the receptors published to date does by far not explain the enormous number of bitter tastants recognised by the mammalian gustatory system. Also very little is known about substances that can act as antagonists of bitter taste receptors and thereby reduce or suppress a bitter taste sensation.

The knowledge about compounds that act as bitter receptor antagonists is prerequisite to the implementation of a method to isolate structurally related antagonists which may be at least as potent in suppressing the bitter taste receptor activity as the original antagonist and which may feature additional advantages such as lower toxicity, better solubility, improved stability and so forth. A bitter taste receptor antagonist isolated by such method can also be isolated and modified or combined with other bitter taste receptor antagonists in such a way that it is capable of targeting a broader range of known bitter taste receptors with high affinity to achieve a more effective suppression of bitter taste.

The present invention provides compounds which act as agonists of human bitter taste receptor hTAS2R49 function. The disclosure of the present patent application allows the implementation of a method to isolate additional structurally related antagonists or agonists for the bitter taste receptor hTAS2R49 to suppress or to enhance, respectively, bitter taste. Furthermore, the use of such antagonist and agonist is disclosed.

SUMMARY OF THE INVENTION

In a first aspect the present invention relates to a method for isolating/identifying an antagonist of hTAS2R49 bitter taste receptor activity, wherein the bitter taste receptor is encoded by a polynucleotide selected from the group consisting of: (a) polynucleotide encoding at least the mature form of the polypeptide having the amino acid sequence as shown in SEQ ID NO: 2; (b) polynucleotide having the coding nucleotide sequence as shown in SEQ ID NO: 1 encoding at least the mature form of the polypeptide; (c) polynucleotide encoding a fragment or variant of a polypeptide encoded by a polynucleotide of any one of (a) to (b), wherein in said variant one or more amino acid residues are conservatively substituted compared to said polypeptide, and said fragment or variant has hTAS2R49 bitter taste receptor activity; (d) polynucleotide which is an ortholog of the polynucleotide sequences shown in SEQ ID NO: 1 encoding at least the mature form of the corresponding bitter taste receptor; (e) polynucleotide which encodes a polypeptide having hTAS2R49 bitter taste receptor activity, and where said polypeptide is at least 80% identical to a polypeptide as shown in SEQ ID NO: 2; and (f) polynucleotide the complementary strand of which hybridizes under stringent conditions to a polynucleotide as defined in any one of (a) to (e) and which codes for a polypeptide having hTAS2R49 bitter taste receptor activity; comprising the steps: (1) contacting a bitter taste receptor encoded by said polynucleotide or a host cell genetically engineered with said polynucleotide or with a vector containing said polynucleotide to express said bitter taste receptor with a potential antagonist or a pharmaceutically acceptable salt thereof; and (2) determining whether the potential antagonist inhibits the bitter taste receptor activity; wherein prior, concomitantly and/or after step (1) said bitter taste receptor or said host cell is contacted with an agonist of bitter taste receptor hTAS2R49, said agonist being selected from the group consisting of (I) cromolyn (formula I)

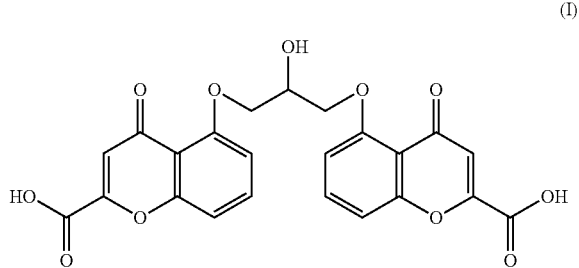 [SMILES: O=C(O)c1cc(=O)c2c(OCC(O)COc3cccc4oc(C(=O)O)cc(=O)c34)cccc2o1]

(I)

or an agonist of bitter taste receptor hTAS2R49 structurally related to cromolyn; and (II) diphenidol (formula II)

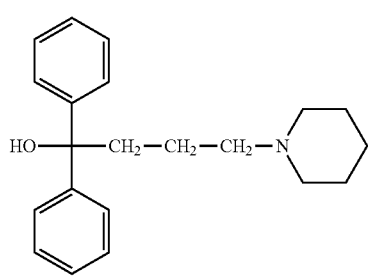

(II)

or an agonist of bitter taste receptor hTAS2R49 structurally related to diphenidol.

In a second aspect the present invention relates to a method for isolating/identifying an agonist of hTAS2R49 bitter taste receptor activity, wherein the bitter taste receptor is encoded by a polynucleotide selected from the group consisting of: (a) polynucleotide encoding at least the mature form of the polypeptide having the amino acid sequence as shown in SEQ ID NO: 2; (b) polynucleotide having the coding nucleotide sequence as shown in SEQ ID NO: 1 encoding at least the mature form of the polypeptide; (c) polynucleotide encoding a fragment or variant of a polypeptide encoded by a polynucleotide of any one of (a) to (b), wherein in said variant one or more amino acid residues are conservatively substituted compared to said polypeptide, and said fragment or variant has hTAS2R49 bitter taste receptor activity; (d) polynucleotide which is an ortholog of the polynucleotide sequences shown in SEQ ID NO: 1 encoding at least the mature form of the corresponding bitter taste receptor; (e) polynucleotide which encodes a polypeptide having hTAS2R49 bitter taste receptor activity, and where said polypeptide is at least 80% identical to a polypeptide as shown in SEQ ID NO: 2; and (f) polynucleotide the complementary strand of which hybridizes under stringent conditions to a polynucleotide as defined in any one of (a) to (e) and which codes for a polypeptide having hTAS2R49 bitter taste receptor activity; comprising the steps: (1) contacting a bitter taste receptor encoded by said polynucleotide or a host cell genetically engineered with said polynucleotide or with a vector containing said polynucleotide to express said bitter taste receptor with a potential agonist that is structurally related to cromolyn or diphenidol; and (2) determining whether the potential agonist induces bitter taste receptor activity.

In a third aspect the present invention relates to a method for the production of a modified agonist of hTAS2R49, wherein an agonist identified in a method according to the second aspect is modified by the addition and/or exchange of at least one substituent.

In a fourth aspect the present invention relates to a method for the production of a modified antagonist of hTAS2R49, wherein an antagonist identified in a method according to the first aspect is modified by the addition and/or exchange of at least one substituent.

In a fifth aspect the present invention relates to a method for the production of food, a food precursor material or additive employed in the production of foodstuff comprising admixing the agonist or antagonist isolated/identified by the method of the second or the first aspect or the modified agonist or antagonist produced according to the method of the third or the fourth aspect or cromolyn or diphenidol with foodstuff, a food precursor material or additive employed in the production of foodstuff.

In a sixth aspect the present invention relates to a method for the production of an animal repellent, precursor material or additive employed in the production of an animal repellent comprising admixing the agonist isolated according to the method of the second aspect, the modified agonist produced according to the method of the third aspect, cromolyn, or diphenidol as active ingredient with an animal repellent or any precursor material or additive employed in the production of an animal repellent.

In a seventh aspect the present invention relates to a method for the production of a nutraceutical or pharmaceutical composition comprising the step of admixing the antagonist isolated/identified by the method of the first aspect or the modified antagonist produced according to the method of the fourth aspect with an active agent and optionally with a pharmaceutically acceptable carrier and/or adjuvant(s).

In an eighth aspect the present invention relates to a foodstuff, any foodstuff precursor material or additive employed in the production of foodstuff producible according to the fifth aspect.

In a ninth aspect the present invention relates to an animal repellent, any precursor material, or additive employed in the production of an animal repellent producible according to the sixth aspect.

In a tenth aspect the present invention relates to a nutraceutical or pharmaceutical composition producible according to the seventh aspect comprising at least one nutraceutically or pharmaceutically active agent, an optional pharmaceutically acceptable carrier and/or adjuvant(s).

In an eleventh aspect the present invention relates to a use of a bitter taste receptor agonist isolated/identified by the method of the second aspect or of a modified agonist producible according to the method of the third aspect to enhance bitter taste.

In a twelfth aspect the present invention relates to a use of a bitter taste receptor antagonist isolated/identified by the method of the first aspect, or of a modified antagonist producible according to the method of the fourth aspect to suppress bitter taste.

In a thirteenth aspect the present invention relates to a use of cromolyn or diphenidol or an agonist of bitter taste receptor activity structurally related to cromolyn or diphenidol to enhance bitter taste.

In a fourteenth aspect the present invention relates to a use of an antagonist of bitter taste receptor activity structurally related to cromolyn or diphenidol to suppress bitter taste.

This summary of the invention does not necessarily describe all features of the invention.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following definitions of the terms: alkyl, heteroalkyl, cycloalkyl, heterocycloalkyl, alicyclic system, aryl, aralkyl, heteroaryl, heteroaralkyl, alkenyl and alkynyl are provided. These terms will in each instance of its use in the remainder of the specification have the respectively defined meaning and preferred meanings.

The term "alkyl" refers to a saturated straight or branched carbon chain. Preferably, the chain comprises from 1 to 10 carbon atoms, i.e. 1, 2, 3, 4, 5, 6, 7, 8, 9 or 10 e.g. methyl, ethyl, propyl (n-propyl or iso-propyl), butyl (n-butyl, iso-butyl, sec-butyl, or tert-butyl), pentyl, hexyl, heptyl, octyl, nonyl, or decyl. Alkyl groups are optionally substituted.

The term "heteroalkyl" refers to a saturated straight or branched carbon chain. Preferably, the chain comprises from 1 to 9 carbon atoms, i.e. 1, 2, 3, 4, 5, 6, 7, 8, 9 e.g. methyl, ethyl, propyl (n-propyl or iso-propyl), butyl (n-butyl, iso-butyl, sec-butyl, or tert-butyl), pentyl, hexyl, heptyl, octyl, nonyl, which is interrupted one or more times, e.g. 1, 2, 3, 4, 5, with the same or different heteroatoms. Preferably the heteroatoms are selected from O, S, and N, e.g. —O—$CH_3$, —S—$CH_3$, —NH—$CH_3$, —$CH_2$—O—$CH_3$, —$CH_2$—O—$C_2H_5$, —$CH_2$—S—$CH_3$, —$CH_2$—S—$C_2H_5$, —$CH_2$—NH—$CH_3$, —$CH_2$—NH—$C_2H_5$, —$C_2H_4$—O—$CH_3$, —$C_2H_4$—O—$C_2H_5$, —$C_2H_4$—S—$CH_3$, —$C_2H_4$—S—$C_2H_5$, —$C_2H_4$—NH—$CH_3$, —$C_2H_4$—NH—$C_2H_5$, etc. Heteroalkyl groups are optionally substituted.

The terms "cycloalkyl" and "heterocycloalkyl", by themselves or in combination with other terms, represent, unless otherwise stated, cyclic versions of "alkyl" and "heteroalkyl", respectively, with preferably 3, 4, 5, 6, 7, 8, 9 or 10 atoms forming a ring, e.g. cyclopropyl, cyclobutyl, cyclopentyl, cyclohexyl, cycloheptyl, cyclooctyl, cyclononyl, cyclodecyl. The terms "cycloalkyl" and "heterocycloalkyl" are also meant to include bicyclic, tricyclic and polycyclic versions thereof. If more than one cyclic ring is present such as in bicyclic, tricyclic and polycyclic versions, then these rings may also comprise one or more aryl- or heteroaryl ring. The term "heterocycloalkyl" preferably refers to a saturated ring having five members of which at least one member is a N, O or S atom and which optionally contains one additional O or one additional N; a saturated ring having six members of which at least one member is a N, O or S atom and which optionally contains one additional O or one additional N or two additional N atoms; or a saturated bicyclic ring having nine or ten members of which at least one member is a N, O or S atom and which optionally contains one or two additional O or one, two or three additional N atoms. "Cycloalkyl" and "heterocycloalkyl" groups are optionally substituted. Additionally, for heterocycloalkyl, a heteroatom can occupy the position at which the heterocycle is attached to the remainder of the molecule. Preferred examples of cycloalkyl include $C_3$-$C_{10}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, or decahydro-naphthalenyl. Preferred examples of heterocycloalkyl include $C_3$-$C_{10}$-heterocycloalkyl, in particular 1-(1,2,5,6-tetrahydropyridyl), 1-piperidinyl, 2-piperidinyl, 3-piperidinyl, 4-morpholinyl, 3-morpholinyl, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, 1-piperazinyl, or 2-piperazinyl.

The term "alicyclic system" refers to mono, bicyclic, tricyclic or polycyclic versions of a cycloalkyl or heterocycloalkyl comprising at least one double and/or triple bond. However, an alicyclic system is not aromatic or heteroaromatic, i.e. does not have a system of conjugated double bonds/free electron pairs. Thus, the number of double and/or triple bonds maximally allowed in an alicyclic system is determined by the number of ring atoms, e.g. in a ring system with up to 5 ring atoms an alicyclic system comprises up to one double bond, in a ring system with 6 ring atoms the alicyclic system comprises up to two double bonds. Accordingly, the "cycloalkenyl" as defined below is a preferred embodiment of an alicyclic ring system. Alicyclic systems are optionally substituted.

The term "alkoxy" refers to an —O-alkyl group, i.e. to an oxygen atom substituted by a saturated straight or branched carbon chain. Preferably, the chain comprises from 1 to 10 carbon atoms, i.e. 1, 2, 3, 4, 5, 6, 7, 8, 9 or 10. Thus, preferred alkoxy groups are methoxy, ethoxy, propoxy (n-propoxy or iso-propoxy), butoxy (n-butoxy, sec-butoxy, iso-butoxy, or tert-butoxy), pentoxy, hexoxy, heptoxy, octoxy, nonoxy, or decoxy. Alkoxy groups are optionally substituted.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl, anthracenyl, or phenanthrenyl. The aryl group is optionally substituted.

The term "aralkyl" refers to an alkyl moiety, which is substituted by one or more (e.g. 1, 2, 3) aryl, wherein alkyl and aryl have the meaning as outlined above. An example is the benzyl radical. Preferably, in this context the alkyl chain comprises from 1 to 8 carbon atoms, i.e. 1, 2, 3, 4, 5, 6, 7, or 8, e.g. methyl, ethyl, propyl (n-propyl or iso-propyl), butyl (n-butyl, iso-butyl, sec-butyl, or tert-butyl), pentyl, hexyl, heptyl, octyl. Preferably, in this context the alkyl chain is substituted by one or more (e.g. 1, 2, 3) phenyl groups, by one or more (e.g. 1, 2, 3) naphthyl groups, by one or more (e.g. 1, 2, 3) anthracenyl groups, or by one or more (e.g. 1, 2, 3) phenanthrenyl groups. The aralkyl group is optionally substituted at the alkyl and/or aryl part of the group.

The term "heteroaryl" preferably refers to a five or six-membered aromatic monocyclic ring wherein at least one of the carbon atoms are replaced by 1, 2, 3, or 4 (for the five membered ring) or 1, 2, 3, 4, or 5 (for the six membered ring) of the same or different heteroatoms, preferably selected from O, N and S; an aromatic bicyclic ring system wherein 1, 2, 3, 4, 5, or 6 carbon atoms of the 8, 9, 10, 11 or 12 carbon atoms have been replaced with the same or different heteroatoms, preferably selected from O, N and S; or an aromatic tricyclic ring system wherein 1, 2, 3, 4, 5, or 6 carbon atoms of the 13, 14, 15, or 16 carbon atoms have been replaced with the same or different heteroatoms, preferably selected from O, N and S. Examples are oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothiophenyl, 2-benzothiophenyl, 1H-indazolyl, benzimidazolyl, benzoxazolyl, indoxazinyl, 2,1-benzisoxazoyl, benzothiazolyl, 1,2-benzisothiazolyl, 2,1-benzisothiazolyl, benzotriazolyl, quinolinyl, isoquinolinyl, quinoxalinyl, quinazolinyl, 1,2,3-benzotriazinyl, or 1,2,4-benzotriazinyl.

The term "heteroaralkyl" refers to an alkyl moiety, which is substituted by one or more (e.g. 1, 2, 3) heteroaryl, wherein alkyl and heteroaryl have the meaning as outlined above. An example is the 2-alkylpyridinyl, 3-alkylpyridinyl, or 2-methylpyridinyl. Preferably, in this context the alkyl chain comprises from 1 to 8 carbon atoms, i.e. 1, 2, 3, 4, 5, 6, 7, or 8, e.g. methyl, ethyl, propyl (n-propyl or iso-propyl), butyl (n-butyl, iso-butyl, sec-butyl, or tert-butyl), pentyl, hexyl, heptyl, octyl. The heteroaralkyl group is optionally substituted at the alkyl and/or heteroaryl part of the group.

The terms "alkenyl" and "cycloalkenyl" refer to branched or straight carbon chains containing olefinic unsaturated carbon atoms and to rings with one or more double bonds, respectively. Examples are propenyl and cyclohexenyl. Preferably, the alkenyl chain comprises from 2 to 8 carbon atoms, i.e. 2, 3, 4, 5, 6, 7, or 8, e.g. ethenyl, 1-propenyl, 2-propenyl, iso-propenyl, 1-butenyl, 2-butenyl, 3-butenyl, iso-butenyl, sec-butenyl, tert-butenyl, 1-pentenyl, 2-pentenyl, 3-pentenyl, 4-pentenyl, hexenyl, heptenyl, octenyl. The term "alkenyl" also comprises=$CH_2$, i.e. methenyl, or other alkylidene groups, if the substituent is directly bonded via the double bond. Preferably the cycloalkenyl ring comprises from 3 to 14 carbon atoms, i.e. 3, 4, 5, 6, 7, 8, 9, 10, 11, 12, 13 or 14, e.g. cyclopropenyl, cyclobutenyl, cyclopentenyl, cyclohexenyl, cycloheptenyl, cyclooctenyl, cyclononenyl, cyclodecenyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, bicyclo[4.2.0]octenyl, hexahydro-pentalenyl, hexahydro-indenyl, octahydro-azulenyl, or octahydro-naphthalenyl.

The term "alkynyl" and "cycloalkynyl" refers to branched or straight carbon chains or rings containing unsaturated carbon atoms with one or more triple bonds. An example is the propargyl radical. Preferably, the alkynyl chain comprises from 2 to 8 carbon atoms, i.e. 2, 3, 4, 5, 6, 7, or 8, e.g. ethynyl, 1-propynyl, 2-propynyl, 1-butynyl, 2-butynyl, 3-butynyl, 1-pentynyl, 2-pentynyl, 3-pentynyl, 4-pentynyl, hexynyl, heptynyl, octynyl.

The term "optionally substituted" in each instance if not further specified refers to halogen (in particular F, Cl, Br, or I), —$NO_2$, —CN, —OR''', —NR'R'', —COOR''', —CONR'R'', —NR'COR''', —NR''COR''', —NR'CONR'R'', —NR'$SO_2$A, —COR'''; —$SO_2$NR'R'', —OOCR''', —CR'''R''''OH, R'''OH, and —E;

R' and R'' is each independently selected from the group consisting of hydrogen, alkyl, alkenyl, alkynyl, cycloalkyl, heterocycloalkyl, aryl, aralkyl, and heteroaryl or together form a heteroaryl, or heterocycloalkyl;

R''' and R'''' is each independently selected from the group consisting of hydrogen, alkyl, alkenyl, alkynyl, cycloalkyl, heterocycloalkyl, alkoxy, aryl, aralkyl, heteroaryl, and —NR'R'';

E is selected from the group consisting of alkyl, alkenyl, alkynyl, cycloalkyl, alkoxy, alkoxyalkyl, heterocycloalkyl, an alicyclic system, aryl and heteroaryl; optionally substituted.

The terms "polypeptide" and "protein" are used interchangeably herein and mean any peptide-linked chain of amino acids, regardless of length or post-translational modification.

As used herein, the term protein "variant" is to be understood as a polypeptide which. differs in comparison to the polypeptide from which it is derived by one or more changes in the amino acid sequence. The polypeptide from which a variant is derived is also known as the parent polypeptide.

Typically a variant is constructed artificially, preferably by gene-technological means. Typically, the polypeptide from which the variant is derived is a wild-type protein or wild-type protein domain. However, the variants usable in the present invention may also be derived from homologs, orthologs, or paralogs of the parent polypeptide or from artificially constructed variants, provided that the variant exhibits at least one biological activity of the parent polypeptide. The changes in the amino acid sequence may be amino acid exchanges, insertions, deletions, N-terminal truncations, or C-terminal truncations, or any combination of these changes, which may occur at one or several sites. In preferred embodiments, a variant usable in the present invention exhibits a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the amino acid sequence (i.e. exchanges, insertions, deletions, N-terminal truncations, and/or C-terminal truncations). The amino acid exchanges may be conservative or non-conservative. In preferred embodiments, a variant usable in the present invention differs from the protein or domain from which it is derived by up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acid exchanges, preferably conservative amino acid changes. Variants may additionally or alternatively comprise deletions of amino acids, which may be N-terminal truncations, C-terminal truncations or internal deletions or any combination of these. Such variants comprising N-terminal truncations, C-terminal truncations and/or internal deletions are referred to as "deletion variants" or "fragments" in the context of the present application. The terms "deletion variant" and "fragment" are used interchangeably herein. A deletion variant may be naturally occurring (e.g. splice variants) or it may be constructed artificially, preferably by gene-technological means. Typically, the protein or protein domain from which the deletion variant is derived is a wild-type protein. However, the deletion variants of the present invention may also be derived from homologs, orthologs, or paralogs of the parent polypeptide or from artificially constructed variants, provided that the deletion variants exhibit at least one biological activity of the parent polypeptide. Preferably, a deletion variant (or fragment) has a deletion of up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acids at its N-terminus and/or at its C-terminus and/or internally.

A "variant" as used herein, can alternatively or additionally be characterised by a certain degree of sequence identity to the parent polypeptide from which it is derived. More precisely, a variant in the context of the present invention exhibits "at least 80% sequence identity" to its parent polypeptide. Preferably, the sequence identity is over a continuous stretch of 20, 30, 40, 45, 50, 60, 70, 80, 90, 100 or more amino acids.

The expression "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Preferably, the polypeptide in question and the reference polypeptide exhibit the indicated sequence identity over a continuous stretch of 20, 30, 40, 45, 50, 60, 70, 80, 90, 100 or more amino acids. Preferably, the polynucleotide in question and the reference polynucleotide exhibit the indicated sequence identity over a continuous stretch of 60, 90, 120, 135, 150, 180, 210, 240, 270, 300 or more nucleotides. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise. For example, a peptide sequence consisting of 31 amino acids compared to the amino acids of full length hTAS2R49 according to SEQ ID NO: 2 may exhibit a maximum sequence identity percentage of 10.0% (31:309) while a sequence with a length of 154 amino acids may exhibit a maximum sequence identity percentage of 49.8% (154:309).

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) *Proc. Natl. Acad. Sci. USA* 90: 5873-5877), with hmmalign (HMMER package or with the CLUSTAL algorithm (Thompson, J. D., Higgins, D. G. & Gibson, T. J. (1994) *Nucleic Acids Res.* 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST polynucleotide searches are performed with the BLASTN program, score =100, word length =12, to obtain polynucleotide sequences homologous to hTAS2R49 encoding nucleic acids. BLAST protein searches are performed with the BLASTP program, score =50, word length =3, to obtain amino acid sequences homologous to the hTAS2R49 polypeptide, respectively. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:I54-I62) or Markov random fields. When percentages of sequence identity are referred to in the present application, these percentages are calculated in relation to the full length of the longer sequence, if not specifically indicated otherwise.

"Hybridization" can also be used as a measure of sequence identity or homology between two nucleic acid sequences. A nucleic acid sequence encoding hTAS2R49, or a portion thereof, can be used as a hybridization probe according to standard hybridization techniques. The hybridization of an hTAS2R49 probe to DNA or RNA from a test source (e.g. a mammalian cell) is an indication of the presence of the hTAS2R49 DNA or RNA in the test source. Hybridization conditions are known to those skilled in the art and can be found, for example, in Current Protocols in Molecular Biology, John Wiley & Sons, N.Y., 6.3.1-6.3.6, 1991. "Moderate hybridization conditions" are defined as equivalent to hybridization in 2× sodium chloride/sodium citrate (SSC) at 30° C., followed by a wash in 1X SSC, 0.1% SDS at 50° C. "Highly stringent conditions" are defined as equivalent to hybridization in 6× sodium chloride/sodium citrate (SSC) at 45° C., followed by a wash in 0.2 X SSC, 0.1% SDS at 65° C.

"Non-conservative substitutions" or "non-conservative amino acid exchanges" are defined as exchanges of an amino acid by another amino acid listed in a different group of the six standard amino acid groups shown below:
(1) hydrophobic: Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

"Conservative substitutions" are defined as exchanges of an amino acid by another amino acid listed within the same group of the six standard amino acid groups shown above.

As used herein, the term "derivative" of a polypeptide refers to a polypeptide that has been chemically modified so that it comprises other chemical groups than the 20 naturally occurring amino acids. The polypeptide from which the derivative derives is also known as the parent polypeptide. This parent polypeptide can be a naturally occurring protein but can also be a protein variant as defined above. Chemical modifications of a polypeptide may provide advantageous properties as compared to the parent polypeptide, e.g. one or more of enhanced stability, increased biological half-life, or increased water solubility. Chemical modifications applicable to the derivatives usable in the present invention include without limitation: PEGylation, glycosylation of non-glycosylated parent polypeptides, or the modification of the glycosylation pattern present in the parent polypeptide.

A "biological activity" as used herein, refers to any activity a polypeptide may exhibit, including without limitation: enzymatic activity; binding activity to another compound (e.g. binding to another polypeptide, in particular binding to a receptor, or binding to a nucleic acid); inhibitory activity (e.g. enzyme inhibitory activity); activating activity (e.g. enzyme-activating activity); or toxic effects. It is not required that the variant or derivative exhibits such an activity to the same extent as the parent polypeptide. A variant is regarded as a variant within the context of the present application, if it exhibits the relevant activity to a degree of at least 10% of the activity of the parent polypeptide. Likewise, a derivative is regarded as a derivative within the context of the present application, if it exhibits the relevant biological activity to a degree of at least 10% of the activity of the parent polypeptide. The relevant "biological activity" in the context of the present invention is "bitter taste receptor activity", i.e. the ability of the receptor described herein (hTAS2R49) to be stimulated by bitter substances, such as the bitter receptor agonists described herein (e.g. cromolyn or diphenidol). Assays for determining "bitter taste receptor activity" of the hTAS2R49 polypeptide are described immediately below and in several other passages of this specification.

One way of detecting "hTAS2R49 bitter taste receptor activity" is measuring a change in concentration of an intracellular messenger, e.g. $Ca^{2+}$, $IP_3$, or cAMP. One preferred way of measuring "hTAS2R49 bitter taste receptor activity", is the ability to release intracellular calcium in a heterologous cell expression system like, for example, (HEK293T/G16gust44) cells that stably expresses a chimeric G-protein consisting of $G\alpha16$ and 44 carboxyltermini amino acids of a-gustducin, in response to bitter tastants, which is dependent on the expression of polypeptides encoded by the polynucleotides of the present invention. The amount of intracellular calcium released can be monitored by, for example, the in vitro FLIPR assay described herein but also by the measurement of one of a variety of other parameters including, for example, $IP_3$ or cAMP. Additional ways of measuring G-protein coupled receptor activity are known in the art and comprise without limitation electrophysiological methods, transcription assays, which measure, e.g. activation or repression of reporter genes which are coupled to regulatory sequences regulated via the respective G-protein coupled signalling pathway, such reporter proteins comprise, e.g., CAT or LUC; assays measuring internalization of the receptor; or assays in frog melanophore systems, in which pigment movement in melanophores is used as a readout for the activity of adenylate cyclase or phospholipase C (PLC), which in turn are coupled via G-proteins to exogenously expressed receptors (see, for example, McClintock T. S. et al. (1993) Anal. Biochem. 209: 298-305; McClintock T. S. and Lerner M. R. (1997) Brain Res. Brain, Res. Protoc. 2: 59-68, Potenza MN (1992) Pigment Cell Res. 5: 372-328, and Potenza M. N. (1992) Anal. Biochem. 206: 315-322).

As used herein, the term "modulator of hTAS2R49 bitter taste receptor activity" includes both agonists and antagonists of hTAS2R49 bitter taste receptor activity.

As used herein, the term "cromolyn" (also known as cromoglicic acid or cromoglycate or cromoglicate) refers to the compound according to formula I

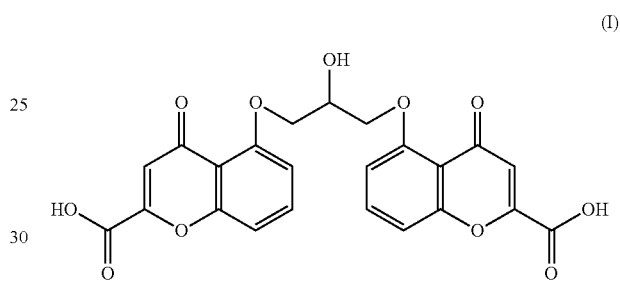

(I)

as well as to pharmaceutically acceptable salts thereof, such as sodium, potassium or ammonium salts. Thus, either or both hydrogen ions at the two carboxy groups may be replaced by sodium, potassium or ammonium ions. As used herein, the term "cromolyn" comprises mixed salts, such as Na—K-cromolyn. A preferred salt of cromolyn usable in the present invention is the disodium salt.

As used herein, the term "diphenidol" refers to the compound according to formula II

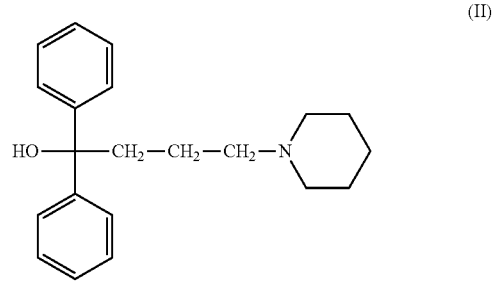 [SMILES: OC(CCCN1CCCCC1)(c1ccccc1)c1ccccc1]

(II)

as well as to pharmaceutically acceptable salts thereof In particular, the nitrogen atom in the piperidine ring system can be protonated and a negatively charged counterion can be associated with the molecule. A preferred salt of diphenidol usable in the present invention is diphenidol HCl.

As used herein, the term "structurally related" refers to a compound which is derived from its corresponding parent compound by 1, 2, 3, 4, 5 or 6 steps of chemical modification. Thus, an agonist or antagonist structurally related to cromolyn is derived from cromolyn by 1, 2, 3, 4, 5 or 6 steps of chemical modification. Likewise, an agonist or antagonist structurally related to diphenidol is derived from diphenidol by 1, 2, 3, 4, 5 or 6 steps of chemical modification. Such chemical modifications include the introduction and/or exchange of one or more substituents.

Such structurally related agonists are further defined in functional terms in that they enhance hTAS2R49 bitter taste receptor activity. In particular, an agonist structurally related to cromolyn or diphenidol stimulates the activity of hTAS2R49 to at least 50% (e.g. at least 60%, 70%, 80%, 90%, 95%, 100%, 110%, 120%, 130%, 140%, 150%, 200%, 250% 300%, 400%, 500%, 1000%) of the activity elicited by cromolyn or diphenidol at the same molar concentration.

The structurally related antagonists are further defined in functional terms in that they inhibit hTAS2R49 bitter taste receptor activity. In particular, an antagonist structurally related to cromolyn or diphenidol lowers the hTAS2R49 bitter taste receptor activity compared to the activity determined in the presence of an hTAS2R49 agonist (e.g. cromolyn or diphenidol), by at least 10% (e.g. at least 10%, 15%, 20%, 30%, 40%, 50%, 60%, 70%, 80%, 90%, 95%, 98%, 99%, 99,5% or 100%). Preferably, the structurally related antagonist exerts this action, when it is contacted prior, concomitantly or after, preferably concomitantly, to the contacting of the hTAS2R49 polypeptide, the host cell expressing the hTAS2R49 polypeptide, or the vector comprising the hTAS2R49 polypeptide, with the hTAS2R49 agonist.

The term "contacting" in the context of the present invention means any interaction between the antagonist and/or agonist with the polypeptide or the host cell, whereby any of the at least two components can be independently of each other in a liquid phase, for example in solution, or in suspension or can be bound to a solid phase, for example, in the form of an essentially planar surface or in the form of particles, beads or the like. In a preferred embodiment a multitude of different compounds are immobilized on a solid surface like, for example, on a compound library chip and the protein of the present invention is subsequently contacted with such a chip; in another preferred embodiment the host cells are genetically engineered with a polynucleotide encoding hTAS2R49, or with a vector containing such a polynucleotide, express the hTAS2R49 bitter taste receptor at the cell surface and are contacted separately in small containers, e. g., micro-titre plates, with various compounds.

As used herein, the term "isolating an antagonist" refers to the process of selecting, identifying, isolating or evolving an antagonist out of a group of at least two different potential antagonists whereby the said selected, identified, isolated or evolved antagonist exhibits preferred features compared with the other antagonists such as, for example, stronger and/or longer or shorter inhibition of receptor activation. Similarly, the term "isolating an agonist" refers to the process of selecting, identifying, isolating or evolving an agonist out of a group of at least two different potential agonists whereby the said selected, identified, isolated or evolved agonist exhibits preferred features compared with the other agonists such as, for example, stronger and/or longer receptor activation.

As used herein, "operatively linked" means incorporated into a genetic construct so that expression control sequences effectively control expression of a coding sequence of interest.

As used herein, "genetically engineered" means that the host cell is transgenic for the polynucleotide or vector containing the polynucleotide.

As used herein, the term "vector" refers to a protein or a polynucleotide or a mixture thereof which is capable of being introduced or of introducing the proteins and/or nucleic acid comprised therein into a cell. In the context of the present invention it is preferred that the proteins encoded by the introduced polynucleotide are expressed within the cell upon introduction of the vector.

A polynucleotide encoding a "mature form" of a protein or polypeptide means that said protein or polypeptide contains all polypeptide elements that allow it to undergo some or all potential post- or cotranslational processes such as proteolytic processing, phosphorylation, lipidation and the like comprised in the state of the art such that said polypeptide or protein can correctly fold and carry out part or all of its wild-type function once it reaches its "mature form".

"Pharmaceutically acceptable" means approved by a regulatory agency of the Federal or a state government or listed in the U.S. Pharmacopeia or other generally recognized pharmacopeia for use in animals, and more particularly in humans.

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The present inventors have identified two agonists, namely cromolyn and diphenidol, which specifically enhance hTAS2R49 human bitter taste receptor (DNA sequence according to SEQ ID NO: 1 and amino acid sequence according to SEQ ID NO: 2) function—an important finding for the food and pharmaceutical industries.

The agonists provided by the present inventors not only enable their use to enhance bitter taste but they also provide the skilled person with a tool to design compound libraries to screen for structurally related agonists to enhance the bitter response of hTAS2R49 human bitter taste receptor, which in turn enables the development of compounds and compositions to enhance bitter tasting components of foods, in particular animal foods, nutrients and dietary supplements and pharmaceutical or homeopathic preparations containing such phytochemicals.

The agonists provided by the present inventors additionally provide the skilled person with a tool to design compound libraries to screen for structurally related antagonists to suppress the bitter response of hTAS2R49 human bitter taste receptor, which in turn enables the development of compounds and compositions to suppress or eliminate bitter tasting components of foods, in particular animal foods, nutrients and dietary supplements and pharmaceutical or homeopathic preparations containing such phytochemicals.

Thus, in a first aspect the present invention is directed to a method for isolating/identifying an antagonist of hTAS2R49 bitter taste receptor activity, wherein the bitter taste receptor is encoded by a polynucleotide selected from the group consisting of:
(a) polynucleotide encoding at least the mature form of the polypeptide having the amino acid sequence as shown in SEQ ID NO: 2;
(b) polynucleotide having the coding nucleotide sequence as shown in SEQ ID NO: 1 encoding at least the mature form of the polypeptide;
(c) polynucleotide encoding a fragment or variant of a polypeptide encoded by a polynucleotide of any one of (a) to (b), wherein in said variant one or more amino acid residues (preferably up to a total number of 50 amino acid residues; e.g. not more than: 50, 45, 40, 35, 30, 25, 20, 15, 14, 13, 12, 11, 10, nine, eight, seven, six, five, four, three, two, or one amino acid residues) are conservatively substituted compared to said polypeptide, and said fragment or variant has hTAS2R49 bitter taste receptor activity;
(d) polynucleotide which is an ortholog of the polynucleotide sequences shown in SEQ ID NO: 1 encoding at least the mature form of the corresponding bitter taste receptor;
(e) polynucleotide which encodes a polypeptide having hTAS2R49 bitter taste receptor activity, and where said polypeptide is at least 80% (e.g. at least 80%, 81%, 82%, 83%, 84%, 85%, 86%, 87%, 88%, 89%, 90%, 91%, 92%, 93%, 94%, 95%, 96%, 97%, 98%, or at least 99%) identical to a polypeptide as shown in SEQ ID NO: 2; and
(f) polynucleotide the complementary strand of which hybridizes under stringent conditions to a polynucleotide as defined in any one of (a) to (e) and which codes for a polypeptide having hTAS2R49 bitter taste receptor activity; comprising the steps:
(1) contacting a bitter taste receptor encoded by said polynucleotide or a host cell genetically engineered with said polynucleotide or with a vector containing said polynucleotide to express said bitter taste receptor with a potential antagonist or a pharmaceutically acceptable salt thereof; and
(2) determining whether the potential antagonist inhibits the bitter taste receptor activity; wherein prior, concomitantly and/or after step (1) said bitter taste receptor or said host cell is contacted with an agonist of bitter taste receptor hTAS2R49, said agonist being selected from the group consisting of
(I) cromolyn (formula I)

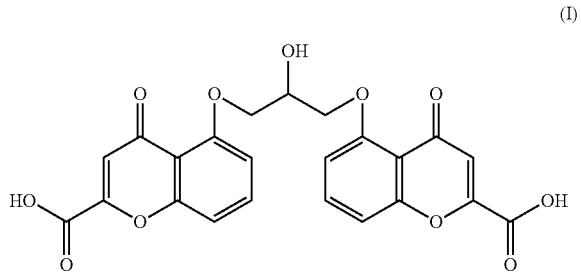 [SMILES: O=C(O)c1cc(=O)c2c(OCC(O)COc3cccc4oc(C(=O)O)cc(=O)c34)cccc2o1]

or an agonist of bitter taste receptor hTAS2R49 structurally related to cromolyn; and
(II) diphenidol (formula II)

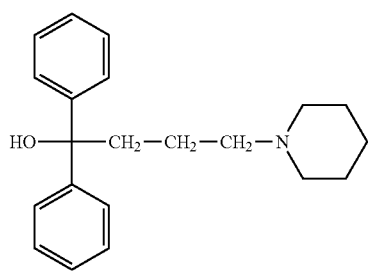

or an agonist of bitter taste receptor hTAS2R49 structurally related to diphenidol.
In a preferred embodiment of the first aspect, the potential antagonist of step (1) is a compound structurally related to cromolyn or structurally related to diphenidol.

In a second aspect the present invention is directed to a method for isolating an agonist of hTAS2R49 bitter taste receptor activity, wherein the bitter taste receptor is encoded by a polynucleotide selected from the group consisting of:
(a) polynucleotide encoding at least the mature form of the polypeptide having the amino acid sequence as shown in SEQ ID NO: 2;
(b) polynucleotide having the coding nucleotide sequence as shown in SEQ ID NO: 1 encoding at least the mature form of the polypeptide;
(c) polynucleotide encoding a fragment or variant of a polypeptide encoded by a polynucleotide of any one of (a) to (b), wherein in said variant one or more amino acid residues (preferably up to a total number of 50 amino acid residues; e.g. not more than: 50, 45, 40, 35, 30, 25, 20, 15, 14, 13, 12, 11, 10, nine, eight, seven, six, five, four, three, two, or one amino acid residues) are conservatively substituted compared to said polypeptide, and said fragment or variant has hTAS2R49 bitter taste receptor activity;
(d) polynucleotide which is an ortholog of the polynucleotide sequences shown in SEQ ID NO: 1 encoding at least the mature form of the corresponding bitter taste receptor;
(e) polynucleotide which encodes a polypeptide having hTAS2R49 bitter taste receptor activity, and where said polypeptide is at least 80% identical (e.g. at least 80%, 81%, 82%, 83%, 84%, 85%, 86%, 87%, 88%, 89%, 90%, 91%, 92%, 93%, 94%, 95%, 96%, 97%, 98%, or at least 99%) to a polypeptide as shown in SEQ ID NO: 2; and
(f) polynucleotide the complementary strand of which hybridizes under stringent conditions to a polynucleotide as defined in any one of (a) to (e) and which codes for a polypeptide having hTAS2R49 bitter taste receptor activity; comprising the steps:
(1) contacting a bitter taste receptor encoded by said polynucleotide or a host cell genetically engineered with said polynucleotide or with a vector containing said polynucleotide to express said bitter taste receptor with a potential agonist that is structurally related to cromolyn or diphenidol; and
(2) determining whether the potential agonist induces bitter taste receptor activity.
In preferred embodiments of the first and the second aspect, the potential antagonist (first aspect) or the potential agonist (second aspect) has a structure according to formula III:

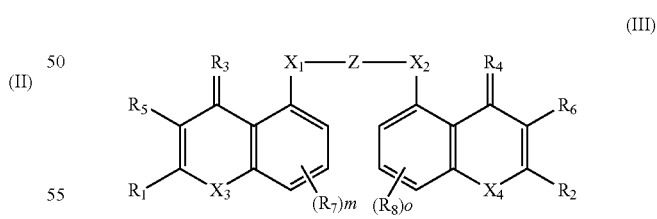

wherein
$X_1$ is O, S, NH, or $CR_9R_{10}$, preferably O or S, most preferably O;
$X_2$ is O, S, NH, or $CR_9R_{10}$, preferably O or S, most preferably O;
$X_3$ is O, S, or NH, most preferably O;
$X_4$ is O, S, or NH, most preferably O;
Z is $(CR_1R_2)_n$;
n is an integer from 0 to 6 (e.g. 0, 1, 2, 3, 4, 5, or 6), preferably 1 to 5, more preferably 2 to 4, most preferably 3;

$R_1$ and $R_2$ are in each instance independently from each other selected from the group consisting of hydrogen; halogen, in particular F, Cl, Br or I; —$NO_2$; —CN; —$OR_{11}$; $NR_{11}R_{12}$; —$COOR_{11}$; —$CONR_{11}R_{12}$; —$NR_9COR_{10}$; —$NR_9CONR_{11}R_{12}$; —$NR_{10}SO_2A$; —$COR_{11}$; —$SO_2NR_{11}R_{12}$; —$OOCR_9$; —$CR_9R_{10}OH$; and —A;

$R_3$ and $R_4$ are independently from each other selected from the group consisting of O, S, or NH, preferably O;

$R_5$ and $R_6$ are independently from each other selected from the group consisting of hydrogen; halogen, in particular F, Cl, Br or I; —$NO_2$; —CN; —$OR_{11}$; —$NR_{11}R_{12}$; —$COOR_{11}$; —$CONR_{11}R_{12}$; —$NR_9COR_{10}$; —$NR_9CONR_{11}R_{12}$; —$NR_{10}SO_2A$; —$COR_{11}$; —$SO_2NR_{11}R_{12}$; —$OOCR_9$; —$CR_9R_{10}OH$; and —A;

$R_7$ and $R_8$ are in each instance independently from each other selected from the group consisting of halogen, in particular F, Cl, Br or I; —$NO_2$; —CN; —$OR_{11}$; —$NR_{11}R_{12}$; —$COOR_{11}$; —$CONR_{11}R_{12}$; —$NR_9COR_{10}$; —$NR_9CONR_{11}R_{12}$; —$NR_{10}SO_2A$; —$COR_{11}$; —$SO_2NR_{11}R_{12}$; —$OOCR_9$; —$CR_9R_{10}OH$; and —A;

m is an integer from 0 to 3; more preferably 0 to 2; even more preferably 0 to 1;

o is an integer from 0 to 3; more preferably 0 to 2; even more preferably 0 to 1;

$R_9$ and $R_{10}$ are in each instance independently from each other selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, n-propoxy, iso-propoxy, butoxy, n-butoxy, sec-butoxy, iso-butoxy, tert-butoxy, pentoxy, or hexoxy; aryl, in particular phenyl, naphthalenyl, anthracenyl, or phenanthrenyl; aralkyl, preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR_{11}R_{12}$; optionally substituted;

$R_{11}$ and $R_{12}$ is in each instance independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, piperazinyl, decahydro-; aryl, in particular phenyl, naphthalenyl, anthracenyl, or phenanthrenyl; aralkyl, preferably $C_1$-$C_6$ aralkyl, e.g. $C_1$, $C_2$, $C_3$, $C_4$, $C_5$, or $C_6$ aralkyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

or $R_{11}$ and $R_{12}$ together form a heteroaryl, heterocycloalkyl, or an alicyclic system comprising one nitrogen atom and optionally comprising one or more further heteroatoms preferably selected from the group consisting of O, S, or N, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, piperazinyl, decahydroquinolinyl, decahydro-isoquinolinyl, decahydro-quinoxalinyl, decahydro-quinazolinyl, 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

A is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, n-propoxy, iso-propoxy, butoxy, n-butoxy, sec-butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl, anthracenyl, or phenanthrenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

or according to formula IV

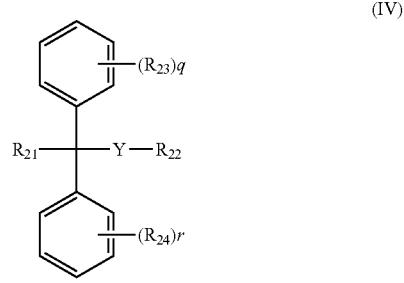

(IV)

wherein

Y is $(CR_{25}R_{26})_p$;

p is an integer from 0 to 6 (e.g. 0, 1, 2, 3, 4, 5, or 6), preferably 1 to 5, more preferably 2 to 4, most preferably 3;

$R_{21}$ is selected from the group consisting of halogen, in particular F, Cl, Br or I; —$NO_2$;

—CN; —$OR_{27}$; —$NR_{27}R_{28}$; —$COOR_{27}$; —$CONR_{27}R_{28}$; —$NR_{25}COR_{26}$; —$NR_{25}CONR_{27}R_{28}$; —$NR_{26}SO_2A$; —$COR_{27}$, —$SO_2NR_{27}R_{28}$; —$OOCR_{25}$; —$CR_{25}R_{26}OH$; and —B;

$R_{22}$ is selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0] octyl, bicyclo[4.2.0]octyl, octahydro-pentalenyl, octahydro-indenyl, decahydro-azulenyl, adamantyl, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro [4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo [2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, n-propoxy, iso-propoxy, butoxy, n-butoxy, sec-butoxy, iso-butoxy, tert-butoxy, pentoxy, or hexoxy; aryl, in particular phenyl, naphthalenyl, anthracenyl, or phenanthrenyl; aralkyl, preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR_{27}R_{28}$; optionally substituted;

$R_{23}$ and $R_{24}$ are in each instance independently from each other selected from the group consisting of halogen, in particular F, Cl, Br or I; —$NO_2$; —CN; —$OR_{27}$; —$NR_{27}R_{28}$; —$COOR_{27}$; —$CONR_{27}R_{28}$; —$NR_{25}COR_{26}$; —$NR_{25}CONR_{27}R_{28}$; —$NR_{26}SO_2B$; —$COR_{27}$; —$SO_2NR_{27}R_{28}$; —$OOCR_{25}$; —$CR_{25}R_{26}OH$; and —B;

q is an integer from 0 to 5, preferably 0 to 4, more preferably 0 to 3, even more preferably 0 to 2, most preferably 0 to 1;

r is an integer from 0 to 5, preferably 0 to 4, more preferably 0 to 3, even more preferably 0 to 2, most preferably 0 to 1; $R_{25}$ and $R_{26}$ are in each instance independently from each other selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, n-propoxy, iso-propoxy, butoxy, n-butoxy, sec-butoxy, iso-butoxy, tert-butoxy, pentoxy, or hexoxy; aryl, in particular phenyl, naphthalenyl, anthracenyl, or phenanthrenyl; aralkyl, preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR_{27}R_{28}$; optionally substituted;

$R_{27}$ and $R_{28}$ are in each instance independently from each other selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl, anthracenyl, or phenanthrenyl; aralkyl, preferably $C_1$-$C_6$ aralkyl, e.g. $C_1$, $C_2$, $C_3$, $C_4$, $C_5$, or $C_6$ aralkyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

or $R_{27}$ and $R_{28}$ together form a heteroaryl, heterocycloalkyl, or an alicyclic system comprising one nitrogen atom and optionally comprising one or more further heteroatoms preferably selected from the group consisting of O, S, or N, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, piperazinyl, decahydroquinolinyl, decahydro-isoquinolinyl, decahydro-quinoxalinyl, decahydro-quinazolinyl, 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted;

B is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3] octyl, spiro[3,5]nonyl, spiro[5,3]nonyl, spiro[3,6]decyl, spiro[6,3]decyl, spiro[4,5]decyl, spiro[5,4] decyl, bicyclo[4.1.0]heptyl, bicyclo[3.2.0]heptyl, bicyclo[2.2.1]heptyl, bicyclo[2.2.2]octyl, bicyclo[5.1.0] octyl, bicyclo[4.2.0]octyl, octahydro-pentalenyl, octahydro-indenyl, decahydro-azulenyl, adamantyl, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, n-propoxy, iso-propoxy, butoxy, n-butoxy, sec-butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl, anthracenyl, or phenanthrenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted.

In preferred embodiments of the first and the second aspect, Z in formula (III) is —$CH_2$—$CH_2$—$CH_2$—, wherein each one of the six hydrogen atoms is optionally substituted by a residue that is in each instance independently selected from the group consisting of halogen, in particular F, Cl, Br or I; —$NO_2$; —CN; —$OR_{11}$; —$NR_{11}R_{12}$; —$COOR_{11}$; —$CONR_{11}R_{12}$; —$NR_9COR_{10}$; —$NR_9CONR_{11}R_{12}$; —$NR_{10}SO_2A$; —$COR_{11}$; —$SO_2NR_{11}R_{12}$; —$OOCR_9$; —$CR_9R_{10}OH$; and —A; wherein $R_9$, $R_{10}$, $R_{11}$, $R_{12}$, and A are defined as above. Preferably, one of the hydrogens atoms at the central —$CH_2$- group is substituted by one of the residues listed in the preceding sentence, preferably by —$OR_{11}$. It is particularly preferred that the central —$CH_2$-group is substituted by —OH or $C_1$-$C_6$ alkoxy, e.g. $C_1$, $C_2$, $C_3$, $C_4$, $C_5$, or $C_6$ alkoxy, preferably methoxy, ethoxy, propoxy (n-propoxy or iso-propoxy), butoxy (n-butoxy, sec-butoxy, iso-butoxy, or tert-butoxy), pentoxy, or hexoxy.

In preferred embodiments of the first and the second aspect, one or both of $X_1$ and $X_2$ are O.

In preferred embodiments of the first and the second aspect, one or both of $X_3$ and $X_4$ are O.

In preferred embodiments of the first and the second aspect, one or both of $R_3$ and $R_4$ are O. In preferred embodiments of the first and the second aspect, each one of $X_3$, $X_4$, $R_3$, and $R_4$ is O.

In preferred embodiments of the first and the second aspect, one or both of $R_1$ and $R_2$ is —$COOR_{11}$, wherein $R_{11}$ is defined as above. In particularly preferred embodiments, $R_{11}$ is hydrogen or alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, or hexyl. The alkyl group may be optionally substituted, wherein the term "optionally substituted" has the meaning as defined in the definition section of this application. In further preferred embodiments, one or both of $R_1$ and $R_2$ is —$COO^-$, wherein the negative charge present at the carboxyl group(s) is compensated by an adequate amount of counter-ions, such as sodium, potassium etc.

In preferred embodiments of the first and the second aspect, $R_{22}$ is —$NR_{29}R_{30}$, wherein $R_{29}$ and $R_{30}$ together form a heteroaryl, heterocycloalkyl, or an alicyclic system comprising one nitrogen atom and optionally comprising one or more further heteroatoms preferably selected from the group consisting of O, S, or N. Preferably, the heteroaryl or heterocycloalkyl or alicyclic system is a five-membered, six-membered, or seven-membered ring, in particular piperidinyl, morpholinyl, 1,3-diazacyclohexane, piperazinyl, 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, or indoxazinyl. Said ring is optionally substituted, preferably 1 to 3 times, by residues that are in each instance independently from each other selected from the group consisting of halogen, in particular F, Cl, Br or I; —$NO_2$, —CN, —$OR_{27}$, —$NR_{27}R_{28}$, —$COOR_{27}$, —$CONR_{27}R_{28}$, —$NR_{25}COR_{26}$, —$NR_{25}CONR_{27}R_{28}$, —NR$_{26}$SO$_2$B, —COR$_{27}$, —SO$_2$NR$_{27}$R$_{28}$, —OOCR$_{25}$, —CR$_{25}$R$_{26}$OH, and —B; wherein R$_{25}$, R$_{26}$, R$_{27}$, R$_{28}$ and B are defined as above.

In preferred embodiments of the first and the second aspect, R$_{22}$ is piperidyl, optionally substituted 1 to 3 times by residues that are in each instance independently from each other selected from the group consisting of halogen, in particular F, Cl, Br or I; —NO$_2$, —CN, —OR$_{27}$, —NR$_{27}$R$_{28}$, —COOR$_{27}$, —CONR$_{27}$R$_{28}$, —NR$_{25}$COR$_{26}$, —NR$_{25}$CONR$_{27}$R$_{28}$, —NR$_{26}$SO$_2$B, —COR$_{27}$, —SO$_2$NR$_{27}$R$_{28}$, —OOCR$_{25}$, —CR$_{25}$R$_{26}$OH, and —B; wherein R$_{25}$, R$_{26}$, R$_{27}$, R$_{28}$ and B are defined as above.

In preferred embodiments of the first and the second aspect, R$_{21}$ is —OR$_{27}$, wherein R$_{27}$ is defined as above. In particularly preferred embodiments R$_{21}$ is —OR$_{27}$, wherein R$_{27}$ is hydrogen or alkyl, in particular C$_1$-C$_6$ alkyl, e.g. C$_1$, C$_2$, C$_3$, C$_4$, C$_5$, or C$_6$ alkyl, preferably methyl, ethyl, propyl (n-propyl or iso-propyl), butyl (n-butyl, sec-butyl, iso-butyl, or tert-butyl), pentyl, or hexyl. The alkyl group can be optionally substituted, wherein the term "optionally substituted" has the meaning as defined in the definition section of this application.

In preferred embodiments of the first and the second aspect, Y is —(CH$_2$)$_p$-, wherein p is an integer from 0 to 6 (e.g. 0, 1, 2, 3, 4, 5, or 6), preferably 1 to 5, more preferably 2 to 4, most preferably 3; and wherein the —(CH$_2$)$_p$- group can be optionally substituted once or twice, wherein the term "optionally substituted" has the meaning as defined in the definition section of this application. In particularly preferred embodiments, Y is —CH$_2$—CH$_2$—CH$_2$—, optionally substituted once or twice.

In preferred embodiments of the first aspect, the potential antagonist having a structure according to formula III is not cromolyn.

In preferred embodiments of the first aspect, the potential antagonist having a structure according to formula IV is not diphenidol.

In preferred embodiments of the second aspect, the identified potential agonist stimulates the activity of hTAS2R49 to at least 50% (e.g. at least 50%, 60%, 70%, 80%, 90%, 95%, 100%, 110%, 120%, 130%, 140%, 150%, 200%, 250% 300%, 400%, 500%, 1000%) of the activity elicited by cromolyn or diphenidol at the same molar concentration.

In preferred embodiments of the first aspect, the identified potential antagonist reduces the activity of hTAS2R49 stimulated by cromolyn or diphenidol at least by 10% (e.g. at least 10%, 15%, 20%, 30%, 40%, 50%, 60%, 70%, 80%, 90%, 95%, 98%, 99%, 99,5% or 100%) at the same molar concentration.

The activity of the receptor described herein can be assessed using a variety of in vitro and in vivo assays to determine functional, chemical, and physical effects, e.g., measuring ligand binding, secondary messengers (e.g., cAMP, cGMP, IP$_3$, DAG, or Ca$^{2+}$) ion flux, phosphorylation levels, transcription levels, of reporter constructs neurotransmitter levels, and the like. Such assays are used in the method of the present invention to test for the activity of the receptors.

The effects of the test compounds upon the function of the receptors can be measured by examining any of the parameters described above. Any suitable physiological change that affects receptor activity can be used to assess the influence of a test compound on the receptors usable in the methods of this invention. When the functional consequences are determined using intact cells or animals, these consequences can be measured by any means known to those skilled in the art, e.g. patch clamping, voltage-sensitive dyes, whole cell currents, radioisotope efflux, inducible markers, oocyte bitter taste receptor gene expression; tissue culture cell bitter taste receptor expression; transcriptional activation of bitter taste receptor genes; ligand binding assays; voltage, membrane potential and conductance changes; ion, preferably sodium or calcium ion flux assays, for example measuring calcium levels using calcium sensitive dyes such as Fluo-3, Fluo-4 or Fura-2; changes in intracellular second messengers such as cAMP, cGMP, and inositol triphosphate (IP$_3$); changes in intracellular calcium levels; neurotransmitter release, and the like. These assays may be performed on intact cells expressing a bitter taste receptor polypeptide, on permeabilized cells, or on membrane fractions produced by standard methods.

Preferred assays for G-protein coupled receptors include cells that are loaded with ion sensitive dyes to report receptor activity. In assays for identifying modulatory compounds, changes in the level of ions in the cytoplasm or membrane voltage will be monitored using an ion sensitive or membrane voltage fluorescent indicator, respectively. For G-protein coupled receptors, promiscuous G-proteins such as Gα15 and Gα16 and chimeric G-proteins can be used in the assay of choice (see, for example, Wilkie et al. (1991) Proc. Nat. Acad. Sci. USA 88: 10049-10053). Such promiscuous G-proteins allow coupling of a wide range of receptors to G-protein dependent signal pathways.

Receptor activation typically initiates subsequent intracellular events, e.g. increases in second messengers such as IP$_3$, which releases intracellular stores of calcium ions. Activation of some G-protein coupled receptors stimulates the formation of inositol trisphosphate through phospholipase C-mediated hydrolysis of phosphatidylinositol bisphosphate (Berridge & Irvine (1984) Nature 312: 315-21). IP$_3$ in turn stimulates the release of intracellular calcium ion stores. Thus, a change in cytoplasmic calcium ion levels, or a change in second messenger levels such as IP$_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EGTA, to distinguish fluorescence response resulting from calcium release from internal stores.

Thus, in preferred embodiments of the first and the second aspect of the invention, hTAS2R49 bitter taste receptor activity is determined by measuring a change in concentration of an intracellular messenger. Preferably the intracellular messenger is selected from the group consisting of Ca$^{2+}$, 1P$_3$, and cAMP.

In a preferred embodiment, receptor activity is measured by expressing the hTAS2R49 bitter taste receptors in a heterologous cell with a G-protein, such as Gα15, Gα16, transducin, gustducin, or a chimeric G-protein that links the receptor to a phospholipase C signal transduction pathway. In another aspect of the invention, only the extracellular domain of the respective bitter taste receptor is expressed as a chimeric transmembrane fusion protein. A preferred cell line is HEK-293, although other mammalian cell lines are also preferred such as CHO and COS cells. Modulation of taste transduction is assayed by measuring changes in intracellular Ca$^{2+}$ levels, which change in response to modulation of the receptor signal transduction pathway via administration of a molecule that associates with the receptor. Changes in Ca$^{2+}$ levels are optionally measured using fluorescent Ca$^{2+}$ indicator dyes and fluorometric imaging. The activity of the signalling molecule and the increase or decrease of that activity in response to the potential antagonist can be determined as outlined above with respect to the identification of bitter taste receptor taste activity. The respectively indicated percent decreases of the activity, which are required to qualify as antagonist, do apply mutatis mutandis. Additionally the term "contacting" has the meaning as outlined above. Preferably the signalling molecule and/or the promiscuous G-protein have been introduced into the cell. The types of cell lines, which are preferred are those indicated below.

In yet another embodiment, the ligand-binding domains of the receptors can be employed in vitro in soluble or solid-state reactions to assay for ligand binding. Ligand binding to a bitter taste receptor, or a domain of a bitter taste receptor, such as e.g. the extracellular domain, can be tested in solution, in a bilayer membrane attached to a solid phase, in a lipid monolayer or vesicles. Thereby, the binding of a modulator to the receptor, or domain, can be observed using changes in spectroscopic characteristics, e.g. fluorescence, fluorescence polarization, plasmon resonance, absorbance or refractive index; or hydrodynamic (e.g. shape), chromatographic, or solubility properties, as is generally known in the art.

The polynucleotide employed in the first and the second aspect of the present invention encodes a polypeptide that still exhibits essentially the same activity as the mature hTAS2R49 bitter taste receptor, respectively, i.e. has "bitter taste receptor activity". Preferably the polypeptide has at least 10% (e.g., at least: 10%, 20%; 30%; 40%; 50%; 60%; 70%; 80%; 90%; 95%; 98%; 99%; 99.5%; or 100% or even more) of the activity of the full-length mature hTAS2R49. The amnio acid sequence of full length hTAS2R49 is shown in SEQ ID NO: 2.

The hTAS2R49 polynucleotide molecule usable in the first or second aspect of the present invention can be DNA, cDNA, genomic DNA, synthetic DNA, or RNA, and can be double-stranded or single-stranded, the sense and/or an antisense strand. Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription.

The polynucleotide molecules usable in the first or second aspect of the present invention can contain naturally occurring sequences, or sequences that differ from those that occur naturally, but, due to the degeneracy of the genetic code, encode the same polypeptide (for example, the polypeptide as shown in SEQ ID NO: 2). In addition, these nucleic acid molecules are not limited to coding sequences, e.g., they can include some or all of the non-coding sequences that lie upstream or downstream from a coding sequence.

The polynucleotide molecules of the invention can be synthesized in vitro (for example, by phosphoramidite-based synthesis) or obtained from a cell, such as the cell of a bacterium or a mammal. The nucleic acids can be those of a human but also include orthologous polynucleotides derived from a non-human primate, mouse, rat, guinea pig, cow, sheep, horse, pig, rabbit, dog, or cat as long as they fulfil the criteria set out above. Combinations or modifications of the polynucleotides within these types of nucleic acids are also encompassed. Means to identify orthologous polynucleotide molecules of the invention are available to a person of skill in the art and comprise the use of BLAST searches (see above) and database mining of databases such as the EMBL, NCBI and other databases comprising polynucleotides and amino acid sequences.

In addition, the polynucleotides usable in the first or second aspect of the present invention can encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location). Recombinant nucleic acid molecules and uses therefore are discussed further below.

In certain preferred embodiments, the method according to the first or second aspect of the present invention uses isolated nucleic acid molecules which are at least 50% (or 55%, 60%, 65%, 70%, 75%, 80%, 85%, 90%, 95%, or 98%) identical to: (a) a nucleic acid molecule that encodes the polypeptide of SEQ ID NO: 2; (b) the polynucleotide sequence of SEQ ID NO: 1 and (c) a nucleic acid molecule which includes a segment of at least 30 (e.g., at least 30, 40, 50, 60, 80, 100, 125, 150, 175, 200, 250, 300, 400, 500, 600, 700, 800, 850, and 900) contiguous nucleotides of SEQ ID NO: 1, in as long as these nucleic acid molecules encode a polypeptide having hTAS2R49 bitter taste receptor activity.

The polynucleotides or proteins useable in the first or second aspect of the present invention can be comprised in a vector containing the polynucleotide(s) or a protein encoded by above-mentioned polynucleotide.

In a preferred embodiment a vector useable in the methods of the present invention comprises plasmids, phagemids, phages, cosmids, artificial mammalian chromosomes, knock-out or knock-in constructs, viruses, in particular adenoviruses, vaccinia viruses, attenuated vaccinia viruses, canary pox viruses, lentivirus (Chang, L J. and Gay, E. E. (2001) Curr. Gene Therap. 1: 237-251), herpes viruses, in particular Herpes simplex virus (HSV-I, Carlezon, W. A. et al. (2000) Crit. Rev. Neurobiol. 14: 47-67), baculovirus, retrovirus, adeno-associated-virus (AAV, Carter, P J. and Samulski, R J. (2000) J. Mol. Med. 6:17-27), rhinovirus, human immune deficiency virus (HIV), filovirus and engineered versions thereof (see, for example, Cobinger G. P. et al. (2001) Nat. Biotechnol. 19:225-30), virosomes, "naked" DNA liposomes, and nucleic acid coated particles, in particular gold spheres. Particularly preferred are viral vectors like adenoviral vectors or retroviral vectors (Lindemann et al. (1997) Mol. Med. 3: 466-76 and Springer et al. (1998) Mol. Cell. 2: 549-58). Liposomes are usually small unilamellar or multilamellar vesicles made of cationic, neutral and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, DOTMA (1, 2-Dioleoyloxypropyl-3-trimethylammoniumbromide) and DOPE (Dioleoyl-phosphatidylethanolamin) which both have been used on a variety of cell lines.

Nucleic acid coated particles are another means for the introduction of nucleic acids into cells using so called "gene guns", which allow the mechanical introduction of particles into cells. Preferably the particles itself are inert, and therefore, are in a preferred embodiment made out of gold spheres.

In a further embodiment polynucleotides usable in the first or second aspect of the present invention are operatively linked to expression control sequences allowing expression in prokaryotic and/or eukaryotic host cells. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression like, for example, promoters transcribed by RNA polymerase III like, e.g. promoters for the snRNA U6 or scRNA 7SK gene, the cytomegalovirus hCMV immediate early gene, the early or late promoters of SV40 adenovirus, viral promoter and activator sequences derived from, e.g. NBV, HCV, HSV, HPV, EBV, HTLV, MMTV or HIV; which allow inducible expression like, for example, CUP-I promoter, the tet-repressor as employed, for example, in the tet-on or tet-off systems, the lac system, the trp, system; regulatory elements directing tissue specific expression, preferably taste bud specific expression, e.g. PLCβ2 promoter or gustducin promoter, regulatory elements directing cell cycle specific expression like, for example, cdc2, cdc25C or cyclin A; or the TAC system, the TRC system, the major operator and promoter regions of phage A, the control regions of fd coat protein, the promoter for 3-phosphoglycerate kinase, the promoters of acid phosphatase, and the promoters of the yeast α- or a-mating factors.

Similarly, the polynucleotides usable in the first and second aspect of the present invention can form part of a hybrid gene encoding additional polypeptide sequences, for example, a sequence that functions as a marker or reporter. Examples of marker and reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyl-transferase (XGPRT). As with many of the standard procedures associated with the practice of the method of the invention, skilled artisans will be aware of additional useful reagents, for example, additional sequences that can serve the function of a marker or reporter.

The methods according to the first and second aspect of the present invention may also use hybrid polypeptides or polynucleotides encoding them. In general a hybrid polypeptide will include a first portion and a second portion; the first portion being one or more hTAS2R49 polypeptide and the second portion being, for example, the reporter(s) described above or an Ig constant region or part of an Ig constant region, e.g. the CH2 and CH3 domains of IgG2a heavy chain. Other hybrids could include an antigenic tag or His tag to facilitate purification and/or detection. Recombinant nucleic acid molecules can also contain a polynucleotide sequence encoding the hTAS2R49 polypeptide operatively linked to a heterologous signal sequence. Such signal sequences can direct the protein to different compartments within the cell and are well known to someone of skill in the art. A preferred signal sequence is a sequence that facilitates secretion of the resulting protein.

In order to express cDNAs encoding the receptors, one typically subclones receptor cDNA into an expression vector that contains a strong promoter to direct transcription, a transcription/translation terminator, and a ribosome-binding site for translational initiation. Suitable bacterial promoters are well known in the art, e.g., *E. coli, Bacillus* sp., and *Salmonella*, and kits for such expression systems are commercially available. Similarly eukaryotic expression systems for mammalian cells, yeast, and insect cells are well known in the art and are also commercially available. The eukaryotic expression vector may be, for example an adenoviral vector, an adeno- associated vector, or a retroviral vector.

In addition to the promoter, the expression vector typically contains a transcription unit or expression cassette that contains all the additional elements required for the expression of the receptor-encoding nucleic acid in host cells. A typical expression cassette thus contains a promoter operatively linked to the nucleic acid sequence encoding the receptor and signals required for efficient polyadenylation of the transcript, ribosome binding sites, and translation termination.

The nucleic acid sequence encoding the receptor may typically be linked to a membrane-targeting signal such as the N-terminal 45 amino acids of the rat somatostatin receptor 3 sequence to promote efficient cell-surface expression of the recombinant receptor. Additional elements of the cassette may include, for example enhancers. An expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ, but there are many more known in the art to the skilled person that can be usefully employed.

Expression vectors containing regulatory elements from eukaryotic viruses are typically used in eukaryotic expression vectors, e.g. SV40 vectors, papilloma virus vectors, and vectors derived from Epstein—Barr virus. Other exemplary eukaryotic vectors include pMSG, pAV009/A.sup.+, pMTO10/A.sup.+, pMAMneo-5, baculovirus pDSVE, pcDNA3.1, pIRES and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable.

The elements that are typically included in expression vectors also include a replicon that functions in *E. coli*, a gene encoding drug resistance to permit selection of bacteria that harbour recombinant plasmids, and unique restriction sites in nonessential regions of the plasmid to allow insertion of eukaryotic sequences. The particular drug resistance gene chosen is not critical; any of the many drug resistance genes known in the art are suitable. The prokaryotic sequences are optionally chosen such that they do not interfere with the replication of the DNA in eukaryotic cells, if necessary.

Standard transfection methods can be used to produce bacterial, mammalian, yeast or insect cell lines that express large quantities of the receptor, which are then purified using standard techniques. Any of the well-known procedures for introducing foreign polynucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing the receptor.

After the expression vector is introduced into the cells, the transfected cells may be cultured under conditions favouring expression of the receptor, which is recovered from the culture using standard techniques. For example the cells may be burst open either mechanically or by osmotic shock before being subject to precipitation and chromatography steps, the nature and sequence of which will depend on the particular recombinant material to be recovered. Alternatively, the recombinant protein may be recovered from the culture medium in which the recombinant cells had been cultured.

In preferred embodiments of the present invention, a host cell genetically engineered with a polynucleotide or a vector as outlined above is used. The host cells that may be used in the methods of the present invention include but are not limited to prokaryotic cells such as bacteria (for example, *E. coli* and *B. subtilis*), which can be transformed with, for example, recombinant bacteriophage DNA, plasmid DNA, or cosmid DNA expression vectors containing the polynucleotide molecules of the invention; simple eukaryotic cells like yeast (for example, *Saccharomyces* and *Pichia*), which can be transformed with, for example, recombinant yeast expression vectors containing the polynucleotide molecule of the invention; insect cell systems like, for example, Sf9 or Hi5 cells, which can be infected with, for example, recombinant virus expression vectors (for example, baculovirus) containing the polynucleotide molecules; amphibian cells, e.g. *Xenopus* oocytes, which can be injected with, for example, plasmids; plant cell systems, which can be infected with, for example, recombinant virus expression vectors (for example, cauliflower mosaic virus (CaMV) or tobacco mosaic virus (TMV)) or transformed with recombinant plasmid expression vectors (for example, Ti plasmid) containing a hTAS2R49 polynucleotide sequence; or mammalian cell systems (for example, COS, CHO, BHK, HEK293, VERO, HeLa, MDCK, Wi38, and NIH 3T3 cells), which can be transformed with recombinant expression constructs containing, for example, promoters derived, for example, from the genome of mammalian cells (for example, the metallothionein promoter) from mammalian viruses (for example, the adenovirus late promoter and the vaccinia virus 7.5K promoter) or from bacterial cells (for example, the tet-repressor binding is employed in the tet-on and tet-off systems). Also useful as host cells are primary or secondary cells obtained directly from a mammal and transfected with a plasmid vector or infected with a viral vector. Depending on the host cell and the respective vector used to introduce the polynucleotide of the invention the polynucleotide can integrate, for example, into the chromosome or the mitochondrial DNA or can be maintained extrachromosomally like, for example, episomally or can be only transiently comprised in the cells.

In a preferred embodiment, the hTAS2R49 receptor, expressed by such cells is functional and has bitter taste receptor activity, i.e., upon binding to one or more bitter molecules it triggers an activation pathway in the cell. The cells are preferably mammalian (e.g., human, non-human primate, horse, bovine, sheep, pig, dog, cat, goat, rabbit, mouse, rat, guinea pig, hamster, or gerbil) cells, insect cells, bacterial cells, or fungal (including yeast) cells. The polypeptides usable in the method of the invention include all those disclosed herein and functional fragments of these polypeptides. As used herein, a functional fragment of the hTAS2R49 bitter taste receptor is a fragment of the hTAS2R49 bitter taste receptor, that is shorter than the full-length hTAS2R49 bitter taste receptor polypeptide, but that has at least 10% (e.g. at least: 10%, 20%, 30%, 40%, 50%, 60%, 70%, 80%, 90%, 95%, 98%, 99%, 99.5%, 100%, 150%, 200%, 500%, 1000%, 10000% or even more) of the ability of the full-length hTAS2R49, as shown in SEQ ID NO: 2, to be stimulated by bitter substances such as the bitter receptor agonists described herein (e.g. cromolyn or diphenidol). Binding assays and bitter substances for hTAS2R49 are described above and below. The polypeptides can also include fusion proteins that contain either a full-length hTAS2R49 polypeptide or a functional fragment of it fused to an unrelated amino acid sequence. The unrelated sequences can add further functional domains or signal peptides.

The polypeptides can be any of those described above but with not more than 50 (e.g., not more than: 50, 45, 40, 35, 30, 25, 20, 15, 14, 13, 12, 11, 10, nine, eight, seven, six, five, four, three, two, or one) conservative substitutions as defined above. All that is required of a polypeptide having one or more conservative substitutions is that it has at least 10% (e.g., at least: 10%, 20%; 30%; 40%; 50%; 60%; 70%; 80%; 90%; 95%; 98%; 99%; 99.5%; 100%, 150%, 200%, 500%, 1000%, 10000% or even more) of the ability of the full-length hTAS2R49 to be stimulated by a hTAS2R49 agonist, such as cromolyn or diphenidol.

Polypeptides and fragments of the polypeptides usable in the method of the present invention can be modified, for example, for in vivo use by the addition of blocking agents, at the amino- and/or carboxyl-terminal ends, to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

The compounds tested as modulators, i.e. potential agonists and antagonists, of the receptors can be any small chemical compound, or a biological entity, such as a protein, sugar, nucleic acid or lipid. Typically, test compounds will be small chemical molecules. Typically, a "small molecule" has a molar mass of 1000 g/mol or less, preferably 500 g/mol or less. Essentially any chemical compound can be used as a potential modulator or ligand in the assays of the invention, although knowledge of the ligand specificity of an individual receptor would enable the skilled person to make an intelligent selection of interesting compounds. The assays may be designed to screen large chemical libraries by automating the assay steps and providing compounds from any convenient source to assays, which are typically run in parallel (e.g., in microtiter formats on microtiter plates in robotic assays). The skilled person will understand that there are many suppliers of libraries of chemical compounds.

Assays may be run in high throughput screening methods that involve providing a combinatorial chemical or peptide library containing a large number of potential therapeutic, or tastant compounds (that are potential ligand compounds). Such libraries are then screened in one or more assays, as described herein, to identify those library members (particular chemical species or subclasses) that display a desired characteristic activity. The compounds thus identified can serve as lead compounds to further develop modulators for final products, or can themselves be used as actual modulators. A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art and no more needs to be stated here.

In the high-throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g. 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention.

The term "potential antagonist", preferably comprises substances other than the agonists cromolyn or diphenidol but structurally related to cromolyn or diphenidol in a non-purified, partially purified or purified state. Preferably, the term "potential antagonist", comprises any perceivable chemical substance or combination thereof (other than cromolyn or diphenidol) having a structure according to formula (III) or (N) in a non-purified, partially purified or purified state. The potential antagonist is selected on the basis of its antagonizing behaviour. An "isolated antagonist" of hTAS2R49 bitter taste receptor activity is a substance which reduces the activity of hTAS2R49 stimulated by a hTAS2R49 bitter taste receptor agonist, preferably selected from the group consisting of the agonists (bitter substances) cromolyn and diphenidol. Preferably this reduction is by at least 10% (e.g., at least: 10%; 15%; 20%; 30%; 40%; 50%; 60%; 70%; 80%; 90%; 95%; 98%; 99%; 99.5%; or 100%), preferably at the same molar concentration. The extent of the lowering of the hTAS2R49 bitter taste receptor activity, caused by the antagonist is determined in the presence of said agonist, e.g. one of the compounds indicated above or a structurally related compound, which may be added prior, concomitantly or after addition of the antagonist. Preferably, the identified antagonist exerts this inhibitory activity, if present in the same molar, 2-fold, 5-fold, 10-fold, 50-fold or 100-fold molar concentration as the agonist. In a preferred embodiment, the "potential antagonist" is a compound structurally related to cromolyn or diphenidol.

The term "potential agonist", preferably comprises cromolyn or diphenidol and substances structurally related to cromolyn or diphenidol in a non-purified, partially purified or purified state. Preferably, the term "potential agonist", comprises any perceivable chemical substance or combination thereof having a structure according to formula (III) or (IV) in a non-purified, partially purified or purified state. The potential agonist is selected on the basis of its receptor stimulating behaviour. An "isolated agonist" of hTAS2R49 bitter taste receptor activity is a substance which stimulates the activity of hTAS2R49 to at least 50% (e.g. at least 60%, 70%, 80%, 90%, 95%, 100%, 110%, 120%, 130%, 140%, 150%, 200%, 250% 300%, 400%, 500%, 1000%) of the activity elicited by cromolyn or diphenidol at the same molar concentration. The extent of activation of the hTAS2R49 bitter taste receptor caused by the agonist can be determined by assays described throughout this specification.

In a third aspect the present invention is directed to a method for the production of a modified agonist of hTAS2R49, wherein an agonist identified in a method according to the second aspect is modified by the addition and/or exchange of at least one substituent. Preferably, the agonist is modified by the addition and/or exchange of 1 to 6 (e.g. 1, 2, 3, 4, 5, or 6) substituents. In a preferred embodiment of the third aspect, a modified agonist is selected based on that it stimulates the activity of hTAS2R49 at least as good as the identified agonist at the same molar concentration.

As a further step after measuring the stimulating effect of a potential agonist and after having measured the increase of bitter taste for at least two different potential agonists at least one potential agonist can be selected, for example, on grounds of the detected increase of intracellular release of calcium.

In a fourth aspect the present invention is directed to a method for the production of a modified antagonist of hTAS2R49, wherein an antagonist identified in a method according to the first aspect is modified by the addition and/or exchange of at least one substituent.

Preferably, the antagonist is modified by the addition and/or exchange of 1 to 6 (e.g. 1, 2, 3, 4, 5, or 6) substituents. In a preferred embodiment of the fourth aspect, a modified antagonist is selected based on that it reduces the activity of hTAS2R49 stimulated by an agonist of hTAS2R49 (e.g. cromolyn or diphenidol or an agonist structurally related thereto) at least as good as the previously identified antagonist at the same molar concentration.

As a further step after measuring the antagonizing effect of a potential antagonist and after having measured the decrease of bitter taste for at least two different potential antagonists at least one potential antagonist can be selected, for example, on grounds of the detected decrease of intracellular release of calcium.

Thus, in accordance with the third and fourth aspect of the invention the selected, e.g. isolated, agonist or antagonist, respectively, is chemically modified in a further step. This chemical modification can be effected by a variety of methods known in the art, which include without limitation the introduction of one or more (preferably one, two, three, four, five, or six) substituents and/or the exchange of one or more (preferably one, two, three, four, five, or six) substituents. Preferably, the substituents introduced or exchanged are in each instance independently selected from the group consisting of halogen, in particular F, Cl, Br or I; $-NO_2$; $-CN$; $-OR^c$; $-NR^aR^b$; $-COOR^c$; $-CONR^aR^b$; $-NR^aCOR^c$; $-NR^aCOR^b$; $-NR^aCONR^aR^a$; $-NR^aSO_2D$; $-COR^c$; $-SO_2NR^aR^b$; $-OOCR^c$; $-CR^cR^dOH$; $R^cOH$; and $-D$;

$R^a$ and $R^b$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, isobutyl, or tert-butyl), pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6] decyl, spiro[6,3]decyl, spiro[4,5]decyl, spiro[5,4]decyl, bicyclo[4.1.0]heptyl, bicyclo[3.2.0]heptyl, bicyclo[2.2.1 ]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; heterocycloalkyl, e.g. $C_3$-$C_{14}$- heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1 ,3-diazacyclohexane, 1,8 diazaspiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5]

decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl, anthracenyl, or phenanthrenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^cR^d$;

$R^c$ and $R^d$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; heterocycloalkyl, e.g. $C_3$-$C_{14}$-heterocycloalkyl, e.g. $C_3$, $C_4$, $C_5$, $C_6$, $C_7$,$^8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; aryl, in particular phenyl, naphthalenyl, anthracenyl, or phenanthrenyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted; and D is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5] decyl, 1,7 diaza-spiro-[4,5] decyl, 1,6 diaza-spiro-[4,5] decyl, 2,8 diaza-spiro[4,5] decyl, 2,7 diaza-spiro[4,5] decyl, 2,6 diaza-spiro[4,5] decyl, 1,8 diaza-spiro-[5,4] decyl, 1,7 diaza-spiro-[5,4] decyl, 2,8 diaza-spiro-[5,4] decyl, 2,7 diaza-spiro[5,4] decyl, 3,8 diaza-spiro[5,4] decyl, 3,7 diaza-spiro[5,4] decyl, 1-aza-7,11-dioxo-spiro[5,5] undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl, anthracenyl, or phenanthrenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted.

The antagonist modified in accordance with the fourth aspect is then tested with the method according to the first aspect of the present invention. The modified antagonist is contacted with the hTAS2R49 polypeptide as such or with the polypeptide expressed in a host cell, which has been contacted prior, concomitantly or after step (1) with an agonist of bitter taste receptor hTAS2R49 (e.g. cromolyn or diphenidol or an agonist structurally related thereto) and subsequently inhibition of the bitter taste receptor activity by the modified antagonist is measured. The inhibition of activation of the hTAS2R49 protein can be measured, e.g. by the intracellular calcium release mediated. If needed, the steps of selecting the antagonist, modifying the compound, contacting the antagonist with a polypeptide or a host cell and measuring of the inhibition of the bitter taste receptor activity can be repeated a further time or any given number of times as required. The above described method is also termed "directed evolution" of an antagonist since it involves a multitude of steps including modification and selection, whereby antagonizing compounds are selected in an "evolutionary" process optimizing their capabilities with respect to a particular property, e.g. their ability to inhibit the activity of hTAS2R49, in particular inhibit the intracellular release of calcium. Preferably, a modified antagonist is selected that reduces the activity of hTAS2R49, stimulated by a hTAS2R49 agonist at least as good as the identified antagonist used as basis for the modified antagonist at the same molar concentration. More preferably, the modified antagonist shows a stronger reduction at the same molar concentration, preferably at least a 10% stronger reduction, 20%, 30%, 40%, 50%, 60, or 70% stronger reduction. In a preferred embodiment an antagonist that is structurally related to cromolyn or diphenidol is used in the first round of above stated directed evolution methods.

The agonist modified in accordance with the third aspect is then tested with the method according to the second aspect of the present invention. The modified agonist is contacted with the hTAS2R49 polypeptide as such or with the polypeptide expressed in a host cell and subsequently activation of the bitter taste receptor activity by the modified agonist is measured. The activation of the hTAS2R49 protein can be measured, e.g. by the intracellular calcium release mediated. If needed, the steps of selecting the agonist, modifying the compound, contacting the agonist with a polypeptide or a host cell and measuring of the activation of the bitter taste receptor activity can be repeated a further time or any given number of times as required. The above described method is also termed "directed evolution" of an agonist since it involves a multitude of steps including modification and selection, whereby stimulating compounds are selected in an "evolutionary" process optimizing their capabilities with respect to a particular property, e.g. their ability to activate the activity of hTAS2R49, in particular increase the intracellular release of calcium. Preferably, a modified agonist is selected that enhances the activity of hTAS2R49 at least as good as the identified agonist used as basis for the modified agonist at the same molar concentration. More preferably, the modified agonist shows a stronger activation at the same molar concentration, preferably at least a 10% stronger activation, 20%, 30%, 40%, 50%, 60, or 70% stronger activation. In a preferred embodiment, an agonist selected from the group consisting of cromolyn, diphenidol, or compounds structurally related thereto is used in the first round of above stated directed evolution methods.

The potential agonists and potential antagonists, which are employed in the methods of the present invention, in particular in the methods according to the first, second, third, and fourth aspect of the invention, can be synthesized by methods and standard procedures known to those skilled in the art, i.e. as described in the literature (for example in the standard works, such as Houben-Weyl, Methoden der organischen Chemie [Methods of Organic Chemistry], Georg-Thieme-Verlag, Stuttgart), to be precise under reaction conditions which are known to those skilled in the art and suitable for the said reactions.

Antagonists identified by methods described herein can be administered directly to a human subject to modulate, e.g. inhibit, bitter taste. Alternatively, such compounds can be formulated with other ingredients of preparations to be taken orally, for example, foods, including animal food, and beverages, pharmaceutical or nutraceutical or homeopathic preparations.

Thus, in a fifth aspect the present invention is directed to a method for the production of food, a food precursor material or additive employed in the production of foodstuff comprising admixing the agonist or antagonist isolated by the method of the second or the first aspect or the modified agonist or antagonist produced according to the method of the third or the fourth aspect or cromolyn or diphenidol with foodstuff, a food precursor material or additive employed in the production of foodstuff.

In preferred embodiments of the fifth aspect, an antagonist isolated by the method of the first aspect or the modified antagonist produced according to the method of the fourth aspect is admixed with foodstuff, a food precursor material or additive employed in the production of foodstuff.

In a sixth aspect the present invention is directed to a method for the production of an animal repellent, precursor material or additive employed in the production of an animal repellent comprising admixing the agonist isolated/identified according to the method of the second aspect, the modified agonist produced according to the method of the third aspect or cromolyn or diphenidol as active ingredient with an animal repellent or any precursor material or additive employed in the production of an animal repellent.

Bitter taste is a particular problem when orally administering pharmaceuticals, which often have an unpleasant bitter taste. In particular in elderly persons, children and chronically ill patients this taste can lead to a lack of compliance with a treatment regimen. In addition in veterinary applications the oral administration of bitter tasting pharmaceuticals can be problematic.

Therefore, in a seventh aspect the present invention is directed to a method for the production of a nutraceutical or pharmaceutical composition comprising the step of admixing the antagonist isolated/identified by the method of the first aspect or the modified antagonist produced according to the method of the fourth aspect with an active agent and optionally with a pharmaceutically acceptable carrier and/or adjuvants. Preferably, the method further comprises the step of formulating the pharmaceutical composition into a pharmaceutically acceptable form.

In an eighth aspect the present invention is directed to a foodstuff, any foodstuff precursor material or additive employed in the production of foodstuff producible according to the fifth aspect.

In a ninth aspect the present invention is directed to an animal repellent any precursor material or additive employed in the production of an animal repellent producible according to the sixth aspect.

In a tenth aspect the present invention is directed to a nutraceutical or pharmaceutical composition producible according to the seventh aspect, comprising at least one nutraceutically or pharmaceutically active agent, and optionally pharmaceutically acceptable carriers and/or adjuvant(s). These pharmaceutical and nutraceutical compositions comprise both products for human and animal consumption.

Regarding the fifth, sixth, seventh, eighth, ninth, and tenth aspect of the invention, the amount of compound including an agonist or antagonist of the present invention to be taken orally must be sufficient to effect a beneficial response in the subject, preferably human subject, and will be determined by the efficacy of the particular taste modulators and the existence, nature, and extent of any adverse side-effects that accompany the administration of a particular compound.

In an eleventh aspect the present invention is directed to a use of a bitter taste receptor agonist isolated/identified by the method of the second aspect or of a modified agonist producible according to the method of the third aspect to enhance bitter taste.

In a twelfth aspect the present invention is directed to a use of a bitter taste receptor antagonist isolated/identified by the method of the first aspect or of a modified antagonist producible according to the method of the fourth aspect to suppress bitter taste.

In a thirteenth aspect the present invention is directed to a use of cromolyn or diphenidol or an agonist of bitter taste receptor activity structurally related to cromolyn or diphenidol to enhance bitter taste. In a preferred embodiment of the thirteenth aspect the enhanced bitter taste is mediated by the bitter taste receptor hTAS2R49.

In a fourteenth aspect the present invention is directed to a use of an antagonist of bitter taste receptor activity structurally related to cromolyn or diphenidol to suppress bitter taste. In a preferred embodiment of the fourteenth aspect the bitter taste is suppressed by inhibiting and/or interfering with activation of the bitter taste receptor hTAS2R49.

The following figures and examples are merely illustrative of the present invention and should not be construed to limit the scope of the invention as indicated by the appended claims in any way.

BRIEF DESCRIPTION OF THE TABLES AND FIGURES

Figure 5B:
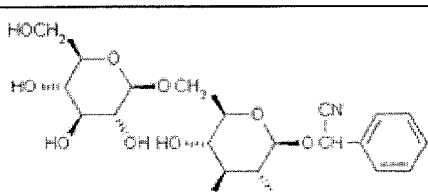
Figure 5B:
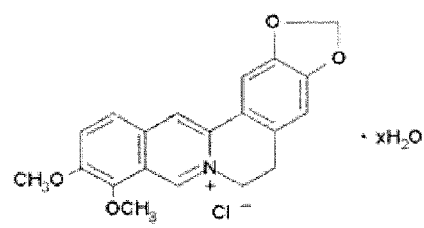
Figure 5B:
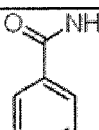
Figure 5B:
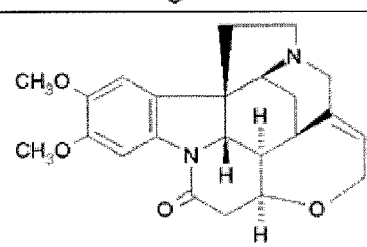
Figure 5B:
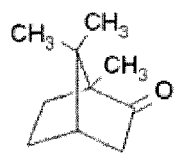
Figure 5B:
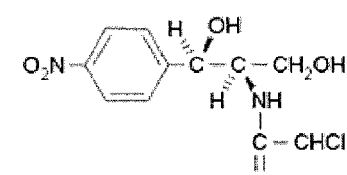

FIG. 5A-5C list substances that do not activate hTAS2R49 in tabular form.

EXAMPLES

Materials
Properties of cromolyn sodium salt (CO399 Sigma):
  inhaled anti-inflammatory agent for the preventive management of asthma
  Cromolyn sodium is the disodium salt of 5,5'-[(2-hydroxytrimethylene)dioxy]bis[4-oxo-4H-1-benzopyran-2-carboxylate]
  Cromolyn sodium is a water-soluble, odorless, white, hydrated crystalline powder
  tasteless at first, but leaves a slightly bitter aftertaste Methods The TAS2R49 human bitter taste receptor was functional expressed in a heterologouse cell system. Therefore, the coding region for this hTAS2R was cloned into a vector (pcDNA5/FRT, Invitrogen, San Diego, Calif.). The construct includes the sequence for the first 45 amino acids of a rat somatostatin receptor type 3 (SST) coupled to the N-terminal end of the receptor for an improvement of receptor membrane targeting. At the C-terminus of the bitter taste receptor a herpes simplex virus glycoprotein D (HSV) epitope was added for immunocytochemical detection. The SST-hTAS2R49-HSV pcDNA5/FRT plasmid construct was transiently transfected into HEK-293T cells stably expressing the chimeric G-protein a subunit Gal6gust44. An empty pcDNA5/FRT plasmid /vector were used as negative control. The cells were seeded into 96-well plates (Greiner Bio-One, Frickenhausen, Germany) under conventional cell culture conditions (Dulbecco's Modified Eagle Medium (DMEM)/10% FCS/1% penicillin/streptomycin; 37° C., 5% CO2, 95% humidity) and 24-26 h later transfected with 150 ng plasmid DNA and 300 ng Lipofectamine 2000 (Invitrogen, San Diego, Calif.). 24-26 h later the cells were loaded with the calcium sensitive dye Fluo4-acetoxymethyl (Molecular Probes, Karlsruhe, Germany) with a final concentration of 20 μM in serum-free DMEM medium. The organic anion-transport inhibitor probenecid (Sigma Aldrich, München, Germany) was added to the dye/medium solution to reduce leakage of the indicator after cleavage of the ester bonds. 1 h after loading, the well plates were washed 3 times with 30 min incubation between the last second wash steps (protected from light) by Denley cell washer (Thermo Fisher Scientific Inc., Waltham, Mass.). The washing solution contains 130 mM NaCl, 5 mM KCl, 10 mM HEPES with pH 7.4, 2 mM $CaCl_2$, and 10 mM Glucose. The agonist was solved and diluted in wash solution.

The elevation of the cytosolic calcium concentration was measured after application of the test substances using the Fluorometric Imaging Plate Reader (FLIPR, Molecular Devices, Munich, Germany) at 510 nm excitation. The vitality of the cells was verified by a second application of 100 nM somatostatin-14, an agonist of the endogenous β-adrenergic somatostatin receptor type 2. To exclude unspecific responses and false positive signals, mock transfected cells were always measured on the same plate with the same compound concentration each. All experiments were performed at least twice. For the calculation of the dose-response function, the signals of the wells with the same concentration of the agonist were automatically normalized with the control wells (mock transfection, $F_{mock}$) by FLIPR384® software (Molecular Devices, Munich, Germany). To consider the dye loading efficiency and the cell number the background fluorescence was measured for each plate/each well and denoted as signal test. The fluorescence counts between the signal minimum and signal maximum ($F_{min.max}$) were divided by the background fluorescence ($F_{signal\ test}$) and were displayed as a ratio=$(F_{min,max}-F_{mock})/F_{signal\ test}$. The calculation of the EC50 values were prepared in SigmaPlot 9.0 by nonlinear regression to the function $f(x)=100/[1+(EC50/x)nH]$, where x is the agonist concentration and nH is the Hill coefficient.

Results

Figure 1:
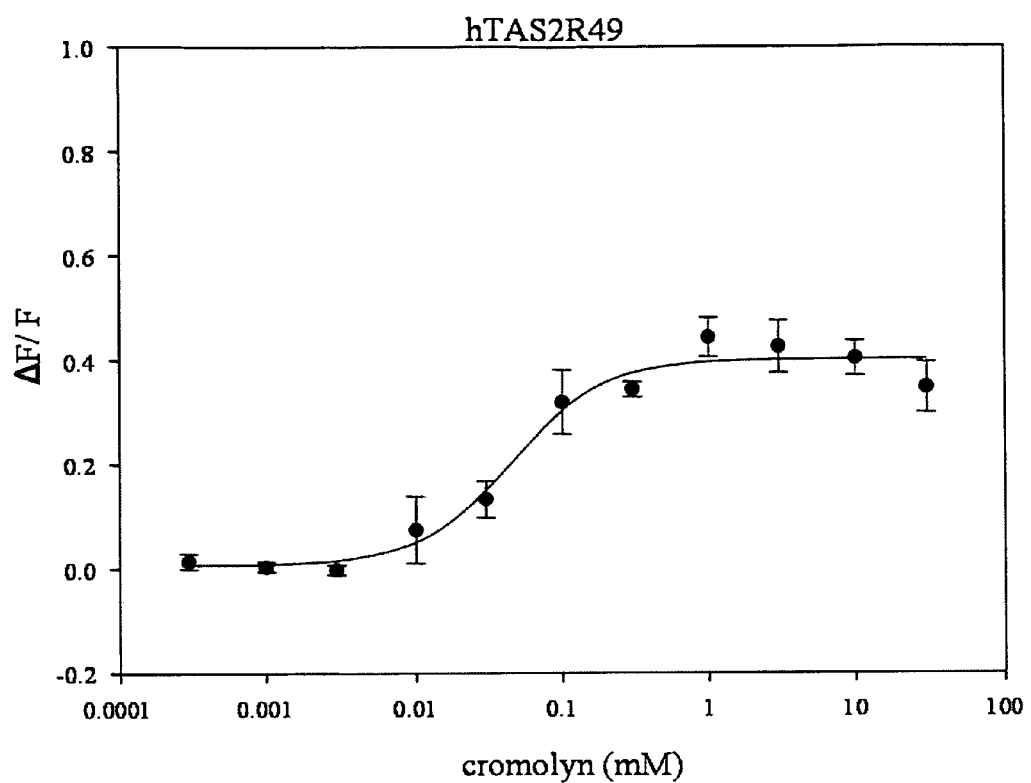
FIG. 1 shows an averaged dose response curve (n=5) for cromolyn. $EC_{50}$=0.042±0.013 mM; threshold ~0.01mM
Figure 2:
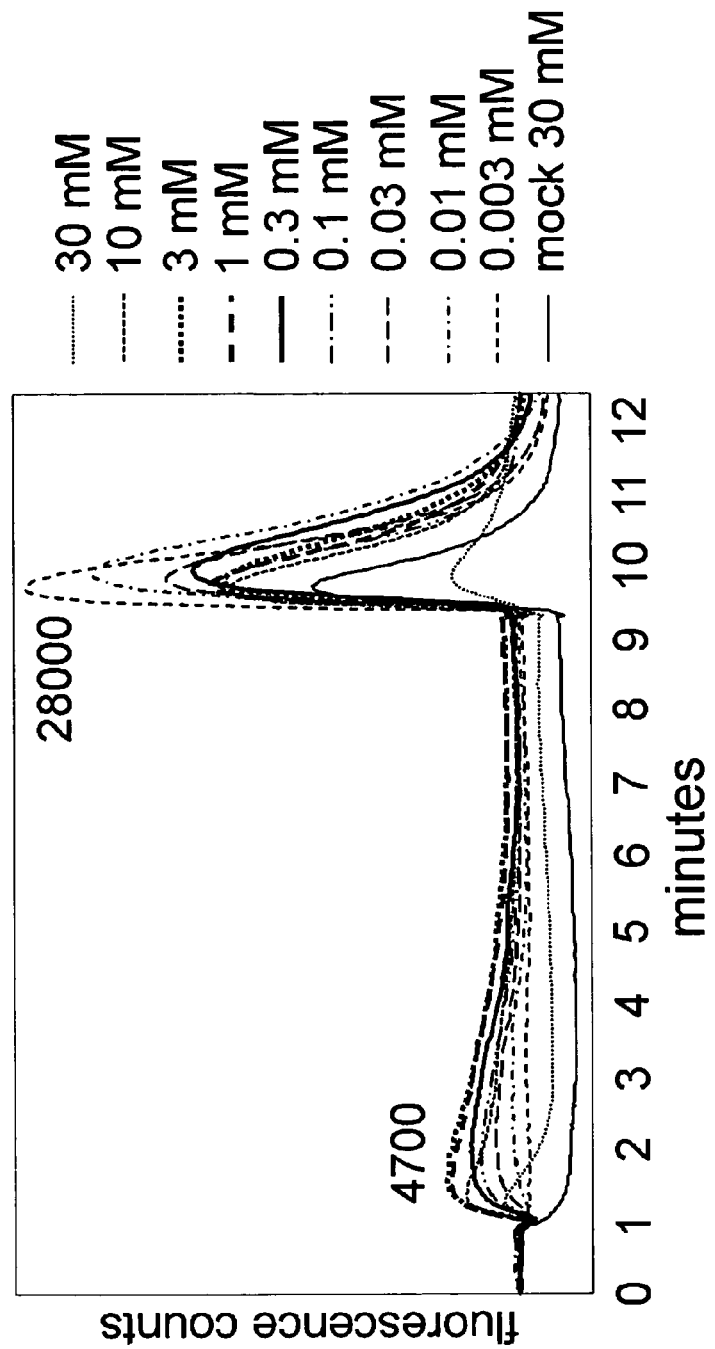
FIG. 2 shows the dose-dependent stimulation of TASR49 by cromolyn in the course of time.
Figure 3:
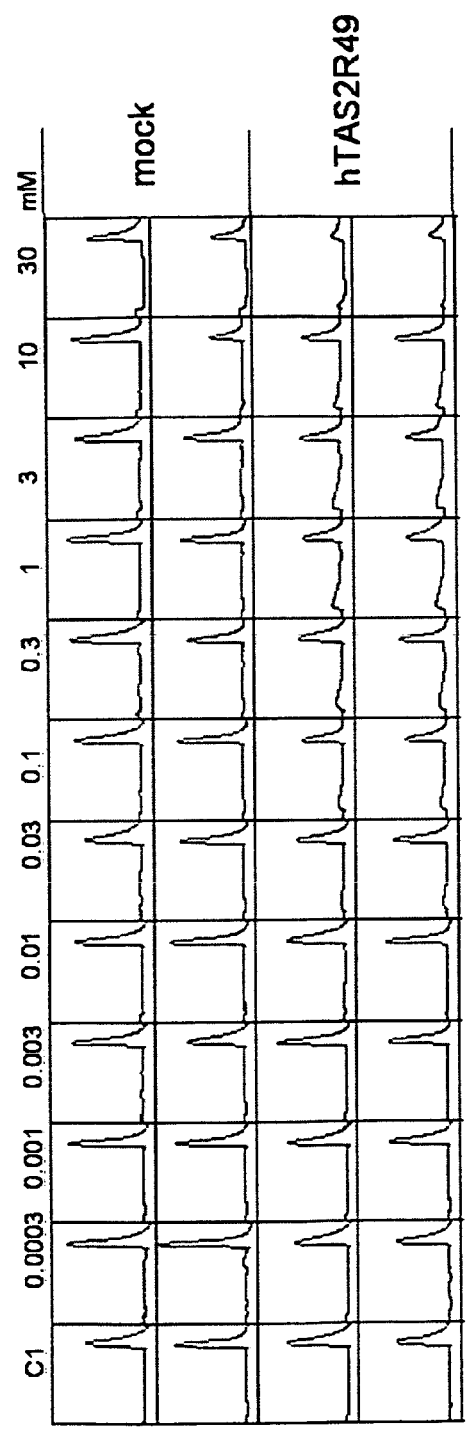
FIG. 3 shows raw FLIPR traces of the application of a concentration series of cromolyn and control application (mock transfection, C1 puffer).
Figure 4:
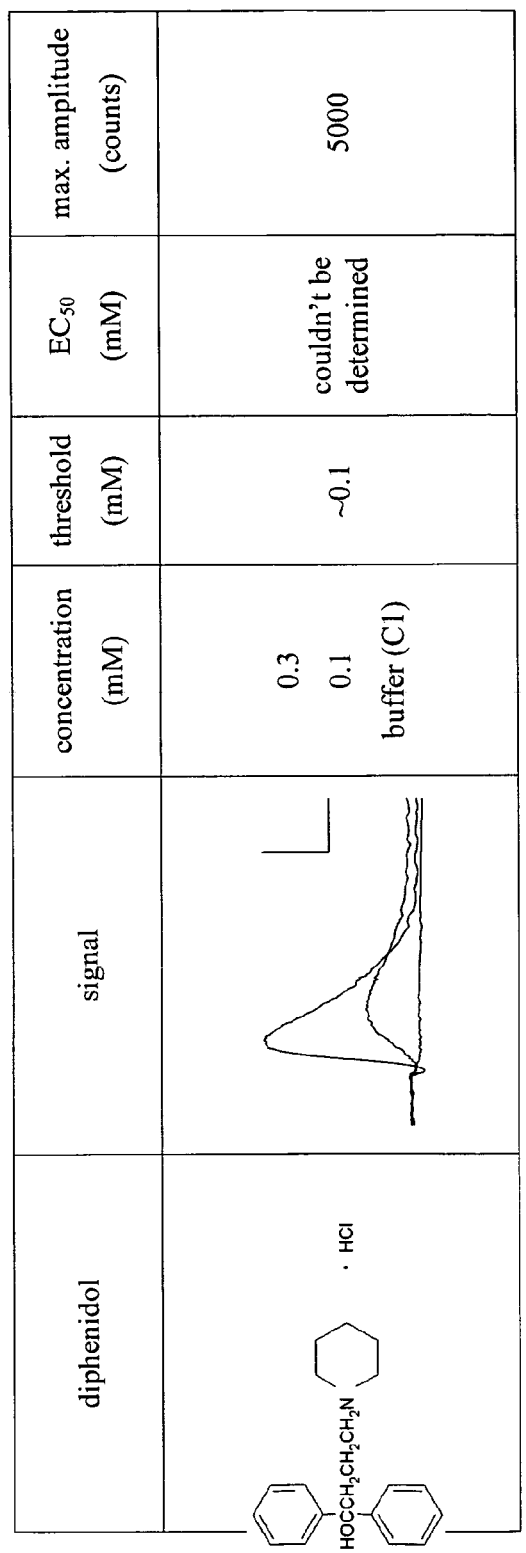
FIG. 4 shows the structure of diphenidol and the response of hTAS2R49 on diphenidol in tabular form (Scale denotes 1 min and 2000 RFU).

The receptor TAS2R49, for which an agonist was hitherto not reported, neither by us nor by others, responded robustly to exposure with cromolyn (FIGS. 1 and 2). FIG. 3 shows the recorded calcium traces (raw data) according to the applied concentration from 0.0003 mM to 30 mM. The buffer (C1 solution) shows no activation, neither the hTAS2R49 nor the mock transfected cells. In addition, the compound diphenidol also activated the receptor. However, in this case we were unable to determine $EC_{50}$ value (FIG. 4). Various other bitter compounds did not stimulate hTAS2R49 (FIG. 5).

Conclusions

We found that cromolyn appears to be an effective agonist of hTAS2R49 with an $EC_{50}$ of 42 ±13 μM. Diphenidol is also an agonist for hTAS2R49. Many other test compounds did not stimulate hTAS2R49.

The invention claimed is:

1. A method for isolating an antagonist of hTAS2R49 bitter taste receptor activity, wherein the bitter taste receptor is encoded by a polynucleotide selected from the group consisting of:
   (a) polynucleotides that encode at least a mature form of the polypeptide having the amino acid sequence as shown in SEQ ID NO: 2;
   (b) polynucleotides that have a coding nucleotide sequence as shown in SEQ ID NO: 1 encoding at least the mature form of the polypeptide;
   (c) polynucleotides that encode a fragment or variant of a polypeptide encoded by a polynucleotide of any one of (a) to (b), wherein in said variant no more than 30 amino acid residues are conservatively substituted compared to a polypeptide encoded by a polynucleotide of any one of (a) to (b) or in said variant no more than 30 amino acids are deleted compared to a polypeptide encoded by a polynucleotide of any one of (a) to (b), and said fragment or variant has hTAS2R49 bitter taste receptor activity;
   (d) polynucleotides that are orthologs of the polynucleotide sequences shown in SEQ ID NO: 1 encoding at least the mature form of the corresponding bitter taste receptor;
   (e) polynucleotides that encode a polypeptide having hTAS2R49 bitter taste receptor activity, and where said polypeptide is at least 90% identical to a polypeptide as shown in SEQ ID NO: 2; and
   (f) polynucleotides the complementary strand of which hybridizes under highly stringent conditions to a polynucleotide as defined in any one of (a) to (e) and which encode a polypeptide having hTAS2R49 bitter taste receptor activity;

comprising the steps:

(1) contacting a bitter taste receptor encoded by said polynucleotide or a cultured host cell genetically engineered with said polynucleotide or with a vector containing said polynucleotide to express said bitter taste receptor with a potential antagonist or a pharmaceutically acceptable salt thereof; and (2) determining whether the potential antagonist inhibits the bitter taste receptor activity;

wherein prior to, concomitantly and/or after step (1) said bitter taste receptor or said cultured host cell is contacted with an agonist of bitter taste receptor hTAS2R49, said agonist being selected from the group consisting of (I) cromolyn (formula I)

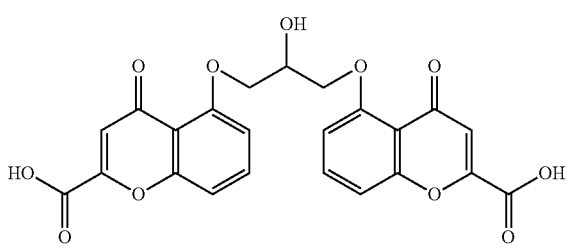

(I)

or an agonist of bitter taste receptor hTAS2R49 structurally related to cromolyn; and (II) diphenidol (formula II)

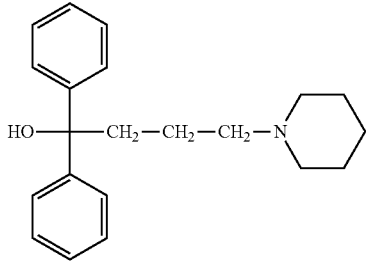

or an agonist of bitter taste receptor hTAS2R49 structurally related to diphenidol.

2. The method of claim 1 wherein the potential antagonist of step (1) is a compound structurally related to cromolyn or structurally related to diphenidol.

3. The method of claim 2, wherein the potential antagonist has a structure according to formula III:

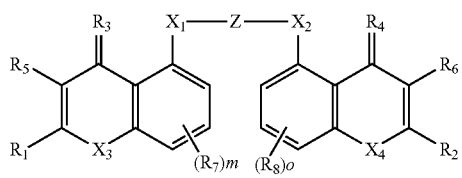

wherein
$X_1$ is O, S, NH, or $CR_9R_{10}$;
$X_2$ is O, S, NH, or $CR_9R_{10}$;
$X_3$ is O, S, or NH;
$X_4$ is O, S, or NH;
Z is $(CR_1R_2)_n$;
n is an integer from 0 to 6;
$R_1$ and $R_2$ are in each instance independently from each other selected from the group consisting of hydrogen, halogen, —$NO_2$, —CN, —$OR_{11}$, —$NR_{11}R_{12}$, —$COOR_{11}$, —$CONR_{11}R_{12}$, —$NR_9COR_{10}$, —$NR_9CONR_{11}R_{12}$, —$NR_{10}SO_2A$, —$COR_{11}$, —$SO_2NR_{11}R_{12}$, —$OOCR_9$, —$CR_9R_{10}OH$, and -A;
$R_3$ and $R_4$ are independently from each other selected from the group consisting of O, S, and NH;
$R_5$ and $R_6$ are independently from each other selected from the group consisting of hydrogen, halogen, —$NO_2$, —CN, —$OR_{11}$, —$NR_{11}R_{12}$, —$COOR_{11}$, —$CONR_{11}R_{12}$, —$NR_9COR_{10}$, —$NR_9CONR_{11}R_{12}$, —$NR_{10}SO_2A$, —$COR_{11}$, —$SO_2NR_{11}R_{12}$, —$OOCR_9$, —$CR_9R_{10}OH$, and —A;
$R_7$ and $R_8$ are in each instance independently from each other selected from the group consisting of halogen, —$NO_2$, —CN, —$OR_{11}$, —$NR_{11}R_{12}$, —$COOR_{11}$, —$CONR_{11}R_{12}$, —$NR_9COR_{10}$, —$NR_9CONR_{11}R_{12}$, —$NR_{10}SO_2A$, —$COR_{11}$, —$SO_2NR_{11}R_{12}$, —$OOCR_9$, —$CR_9R_{10}OH$, and -A;
m is an integer from 0 to 3;
o is an integer from 0 to 3;
$R_9$ and $R_{10}$ are in each instance independently from each other selected from the group consisting of hydrogen, alkyl, alkenyl, alkynyl, cycloalkyl, heterocycloalkyl, alkoxy, aryl, aralkyl, heteroaryl, and —$NR_{11}R_{12}$; optionally substituted;

$R_{11}$ and $R_{12}$ are in each instance independently selected from the group consisting of hydrogen, alkyl, alkenyl, alkynyl, cycloalkyl, heterocycloalkyl, aryl, aralkyl, and heteroaryl or $R_{11}$ and $R_{12}$ together form a heteroaryl, heterocycloalkyl, or an alicyclic system comprising one nitrogen atom and optionally comprising one or more further heteroatoms; optionally substituted;
A is selected from the group consisting of alkyl, alkenyl, alkynyl, cycloalkyl, alkoxy, alkoxyalkyl, heterocycloalkyl, an alicyclic system, aryl and heteroaryl; optionally substituted;
or
according to formula IV

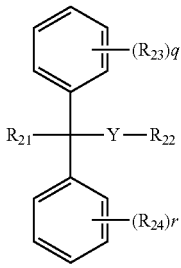

wherein
Y is $(CR_{25}R_{26})_p$;
p is an integer from 0 to 6;
$R_{21}$ is selected from the group consisting of halogen, —$NO_2$, —CN, —$OR_{27}$, —$NR_{27}R_{28}$, —$COOR_{27}$, —$CONR_{27}R_{28}$, —$NR_{25}COR_{26}$, —$NR_{25}CONR_{27}R_{28}$, —$NR_{26}SO_2A$, —$COR_{27}$, —$SO_2NR_{27}R_{28}$, —$OOCR_{25}$, —$CR_{25}R_{26}OH$, and —B;
$R_{22}$ is selected from the group consisting of hydrogen, alkyl, alkenyl, alkynyl, cycloalkyl, heterocycloalkyl, alkoxy, aryl, aralkyl, heteroaryl, and —$NR_{27}R_{28}$; optionally substituted;
$R_{23}$ and $R_{24}$ are in each instance independently from each other selected from the group consisting of halogen, —$NO_2$, —CN, —$OR_{27}$, —$NR_{27}R_{28}$, —$COOR_{27}$, —$CONR_{27}R_{28}$, —$NR_{25}COR_{26}$, —$NR_{25}CONR_{27}R_{28}$, —$NR_{26}SO_2B$, —$COR_{27}$, —$SO_2NR_{27}R_{28}$, —$OOCR_{25}$, —$CR_{25}R_{26}OH$, and —B;
q is an integer from 0 to 5;
r is an integer from 0 to 5;
$R_{25}$ and $R_{26}$ are in each instance independently from each other selected from the group consisting of hydrogen, alkyl, alkenyl, alkynyl, cycloalkyl, heterocycloalkyl, alkoxy, aryl, aralkyl, heteroaryl, and —$NR_{27}R_{28}$; optionally substituted;
$R_{27}$ and $R_{28}$ are in each instance independently from each other selected from the group consisting of hydrogen, alkyl, alkenyl, alkynyl, cycloalkyl, heterocycloalkyl, aryl, aralkyl, and heteroaryl or $R_{27}$ and $R_{28}$ together form a heteroaryl, heterocycloalkyl, or an alicyclic system comprising one nitrogen atom and optionally comprising one or more further heteroatoms; optionally substituted;
B is selected from the group consisting of alkyl, alkenyl, alkynyl, cycloalkyl, alkoxy, alkoxyalkyl, heterocycloalkyl, an alicyclic system, aryl and heteroaryl; optionally substituted.

4. The method of claim 3, wherein Z in formula (III) is —$CH_2$—$CH_2$—$CH_2$—, wherein each one of the six hydrogen atoms is optionally substituted by a residue that is in each instance independently selected from the group consisting of halogen; —NO$_2$; —CN; —OR$_{11}$; —NR$_{11}$R$_{12}$; —COOR$_{11}$; —CONR$_{11}$R$_{12}$; —NR$_9$COR$_{10}$; —NR$_9$CONR$_{11}$R$_{12}$; —NR$_{10}$SO$_2$A; —COR$_{11}$; —SO$_2$NR$_{11}$R$_{12}$; —OOCR$_9$; —CR$_9$R$_{10}$OH; and —A;

wherein R$_9$, R$_{10}$, R$_{11}$, R$_{12}$, and A are defined as in claim 3.

5. The method of claim 3, wherein R$_{22}$ is —NR$_{29}$R$_{30}$, wherein R$_{29}$ and R$_{30}$ together form a heteroaryl, heterocycloalkyl, or an alicyclic system comprising one nitrogen atom and optionally comprising one or more further heteroatoms;

wherein said ring is optionally substituted 1 to 3 times by residues that are in each instance independently from each other selected from the group consisting of halogen, —NO$_2$, —CN, —OR$_{27}$, —NR$_{27}$R$_{28}$, —COOR$_{27}$, —CONR$_{27}$R$_{28}$, —NR$_{25}$COR$_{26}$, —NR$_{25}$CONR$_{27}$R$_{28}$, —NR$_{26}$SO$_2$B, —COR$_{27}$, —SO$_2$NR$_{27}$R$_{28}$, —OOCR$_{25}$, —CR$_{25}$R$_{26}$OH, and —B;

wherein R$_{25}$, R$_{26}$, R$_{27}$, R$_{28}$ and B are defined as in claim 3.

6. The method of claim 3, wherein R$_{22}$ is piperidyl, optionally substituted 1 to 3 times by residues that are in each instance independently from each other selected from the group consisting of halogen, —NO$_2$, —CN, —OR$_{27}$, —NR$_{27}$R$_{28}$, —COOR$_{27}$, —CONR$_{27}$R$_{28}$, —NR$_{25}$COR$_{26}$, —NR$_{25}$CONR$_{27}$R$_{28}$, —NR$_{26}$SO$_2$B, —COR$_{27}$, —SO$_2$NR$_{27}$R$_{28}$, —OOCR$_{25}$, —CR$_{25}$R$_{26}$OH, and —B;

wherein R$_{25}$, R$_{26}$, R$_{27}$, R$_{28}$ and B are defined as in claim 3.

7. The method according to claim 1, wherein the identified potential antagonist reduces the activity of hTAS2R49 stimulated by cromolyn or diphenidol at least by 10% at the same molar concentration.

8. The method according to claim 1, wherein hTAS2R49 bitter taste receptor activity is determined by measuring a change in concentration of an intracellular messenger.

9. The method according to claim 8, wherein the intracellular messenger is selected from the group consisting of Ca$^{2+}$, IP$_3$, and cAMP.

10. The method, according to claim 1, wherein, in part (c), said variant has no more than 15 amino acid substitutions or deletions.

11. A method for isolating an agonist of hTAS2R49 bitter taste receptor activity, wherein the bitter taste receptor is encoded by a polynucleotide selected from the group consisting of:

(a) polynucleotides that encode at least a mature form of the polypeptide having the amino acid sequence as shown in SEQ ID NO: 2;

(b) polynucleotides that have a coding nucleotide sequence as shown in SEQ ID NO: 1 encoding at least the mature form of the polypeptide;

(c) polynucleotides that encode a fragment or variant of a polypeptide encoded by a polynucleotide of any one of (a) to (b), wherein in said variant no more than 30 amino acid residues are conservatively substituted compared to a polypeptide encoded by a polynucleotide of any one of (a) to (b) or in said variant no more than 30 amino acids are deleted compared to a polypeptide encoded by a polynucleotide of any one of (a) to (b), and said fragment or variant has hTAS2R49 bitter taste receptor activity;

(d) polynucleotides that are orthologs of the polynucleotide sequences shown in SEQ ID NO: 1 encoding at least the mature form of the corresponding bitter taste receptor;

(e) polynucleotides that encode a polypeptide having hTAS2R49 bitter taste receptor activity, and where said polypeptide is at least 90% identical to a polypeptide as shown in SEQ ID NO: 2; and (f) polynucleotides the complementary strand of which hybridizes under highly stringent conditions to a polynucleotide as defined in any one of (a) to (e) and which encode a polypeptide having hTAS2R49 bitter taste receptor activity;

comprising the steps:

(1) contacting a bitter taste receptor encoded by said polynucleotide or a cultured host cell genetically engineered with said polynucleotide or with a vector containing said polynucleotide to express said bitter taste receptor with a potential agonist that is structurally related to cromolyn or diphenidol; and (2) determining whether the potential agonist induces bitter taste receptor activity.

12. The method according to claim 11, wherein the identified potential agonist stimulates the activity of hTAS2R49 to at least 50% of the activity elicited by cromolyn or diphenidol at the same molar concentration.

13. The method of claim 11, wherein the potential agonist has a structure according to formula III:

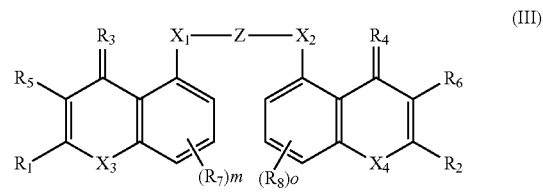

(III)

wherein

X$_1$ is O, S, NH, or CR$_9$R$_{10}$;
X$_2$ is O, S, NH, or CR$_9$R$_{10}$;
X$_3$ is O, S, or NH;
X$_4$ is O, S, or NH;
Z is (CR$_1$R$_2$)$_n$;
n is an integer from 0 to 6;
R$_1$ and R$_2$ are in each instance independently from each other selected from the group consisting of hydrogen, halogen, —NO$_2$, —CN, —OR$_{11}$, —NR$_{11}$R$_{12}$, —COOR$_{11}$, —CONR$_{11}$R$_{12}$, —NR$_9$COR$_{10}$, —NR$_9$CONR$_{11}$R$_{12}$, —NR$_{10}$SO$_2$A, —COR$_{11}$, —SO$_2$NR$_{11}$R$_{12}$, —OOCR$_9$, —CR$_9$R$_{10}$OH, and —A;
R$_3$ and R$_4$ are independently from each other selected from the group consisting of O, S, and NH;
R$_5$ and R$_6$ are independently from each other selected from the group consisting of hydrogen, halogen, —NO$_2$, —CN, —OR$_{11}$, —NR$_{11}$R$_{12}$, —COOR$_{11}$, —CONR$_{11}$R$_{12}$, —NR$_9$COR$_{10}$, —NR$_9$CONR$_{11}$R$_{12}$, —NR$_{10}$SO$_2$A, —COR$_{11}$, —SO$_2$NR$_{11}$R$_{12}$, —OOCR$_9$, —CR$_9$R$_{10}$OH, and —A;
R$_7$ and R$_8$ are in each instance independently from each other selected from the group consisting of halogen, —NO$_2$, —CN, —OR$_{11}$, —NR$_{11}$R$_{12}$, —COOR$_{11}$, —CONR$_{11}$R$_{12}$, —NR$_9$COR$_{10}$, —NR$_9$CONR$_{11}$R$_{12}$, —NR$_{10}$SO$_2$A, —COR$_{11}$, —SO$_2$NR$_{11}$R$_{12}$, —OOCR$_9$, —CR$_9$R$_{10}$OH, and —A;
m is an integer from 0 to 3;
o is an integer from 0 to 3;
R$_9$ and R$_{10}$ are in each instance independently from each other selected from the group consisting of hydrogen, alkyl, alkenyl, alkynyl, cycloalkyl, heterocycloalkyl, alkoxy, aryl, aralkyl, heteroaryl, and —NR$_{11}$R$_{12}$; optionally substituted;
R$_{11}$ and R$_{12}$ are in each instance independently selected from the group consisting of hydrogen, alkyl, alkenyl, alkynyl, cycloalkyl, heterocycloalkyl, aryl, aralkyl, and heteroaryl or $R_{11}$ and $R_{12}$ together form a heteroaryl, heterocycloalkyl, or an alicyclic system comprising one nitrogen atom and optionally comprising one or more further heteroatoms; optionally substituted;

A is selected from the group consisting of alkyl, alkenyl, alkynyl, cycloalkyl, alkoxy, alkoxyalkyl, heterocycloalkyl, an alicyclic system, aryl and heteroaryl; optionally substituted;

or
according to formula IV

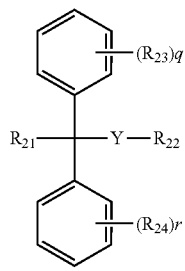

(IV)

wherein

Y is $(CR_{25}R_{26})_p$;

p is an integer from 0 to 6;

$R_{21}$ is selected from the group consisting of halogen, $-NO_2$, $-CN$, $-OR_{27}$, $-NR_{27}R_{28}$, $-COOR_{27}$, $-CONR_{27}R_{28}$, $-NR_{25}COR_{26}$, $-NR_{25}CONR_{27}R_{28}$, $-NR_{26}SO_2A$, $-COR_{27}$, $-SO_2NR_{27}R_{28}$, $-OOCR_{25}$, $-CR_{25}R_{26}OH$, and $-B$;

$R_{22}$ is selected from the group consisting of hydrogen, alkyl, alkenyl, alkynyl, cycloalkyl, heterocycloalkyl, alkoxy, aryl, aralkyl, heteroaryl, and $-NR_{27}R_{28}$; optionally substituted;

$R_{23}$ and $R_{24}$ are in each instance independently from each other selected from the group consisting of halogen, $-NO_2$, $-CN$, $-OR_{27}$, $-NR_{27}R_{28}$, $-COOR_{27}$, $-CONR_{27}R_{28}$, $-NR_{25}COR_{26}$, $-NR_{25}CONR_{27}R_{28}$, $-NR_{26}SO_2B$, $-COR_{27}$, $-SO_2NR_{27}R_{28}$, $-OOCR_{25}$, $-CR_{25}R_{26}OH$, and $-B$;

q is an integer from 0 to 5;

r is an integer from 0 to 5;

$R_{25}$ and $R_{26}$ are in each instance independently from each other selected from the group consisting of hydrogen, alkyl, alkenyl, alkynyl, cycloalkyl, heterocycloalkyl, alkoxy, aryl, aralkyl, heteroaryl, and $-NR_{27}R_{28}$; optionally substituted;

$R_{27}$ and $R_{28}$ are in each instance independently from each other selected from the group consisting of hydrogen, alkyl, alkenyl, alkynyl, cycloalkyl, heterocycloalkyl, aryl, aralkyl, and heteroaryl or $R_{27}$ and $R_{28}$ together form a heteroaryl, heterocycloalkyl, or an alicyclic system comprising one nitrogen atom and optionally comprising one or more further heteroatoms; optionally substituted;

B is selected from the group consisting of alkyl, alkenyl, alkynyl, cycloalkyl, alkoxy, alkoxyalkyl, heterocycloalkyl, an alicyclic system, aryl and heteroaryl; optionally substituted.

14. The method of claim 13, wherein Z in formula (III) is $-CH_2-CH_2-CH_2-$, wherein each one of the six hydrogen atoms is optionally substituted by a residue that is in each instance independently selected from the group consisting of halogen; $-NO_2$; $-CN$; $-OR_{11}$; $-NR_{11}R_{12}$; $-COOR_{11}$; $-CONR_{11}R_{12}$; $-NR_9COR_{10}$; $-NR_9CONR_{11}R_{12}$; $-NR_{10}SO_2A$; $-COR_{11}$; $-SO_2NR_{11}R_{12}$; $-OOCR_9$; $-CR_9R_{10}OH$; and $-A$;

wherein $R_9, R_{10}, R_{11}, R_{12}$, and A are defined as in claim 13.

15. The method of claim 13, wherein $R_{22}$ is $-NR_{29}R_{30}$, wherein $R_{29}$ and $R_{30}$ together form a heteroaryl, heterocycloalkyl, or an alicyclic system comprising one nitrogen atom and optionally comprising one or more further heteroatoms;

wherein said ring is optionally substituted 1 to 3 times by residues that are in each instance independently from each other selected from the group consisting of halogen, $-NO_2$, $-CN$, $-OR_{27}$, $-NR_{27}R_{28}$, $-COOR_{27}$, $-CONR_{27}R_{28}$, $-NR_{25}COR_{26}$, $-NR_{25}CONR_{27}R_{28}$, $-NR_{26}SO_2B$, $-COR_{27}$, $-SO_2NR_{27}R_{28}$, $-OOCR_{25}$, $-CR_{25}R_{26}OH$, and $-B$;

wherein $R_{25}, R_{26}, R_{27}, R_{28}$ and B are defined as in claim 13.

16. The method of claim 13, wherein $R_{22}$ is piperidyl, optionally substituted 1 to 3 times by residues that are in each instance independently from each other selected from the group consisting of halogen, $-NO_2$, $-CN$, $-OR_{27}$, $-NR_{27}R_{28}$, $-COOR_{27}$, $-CONR_{27}R_{28}$, $-NR_{25}COR_{26}$, $-NR_{25}CONR_{27}R_{28}$, $-NR_{26}SO_2B$, $-COR_{27}$, $-SO_2NR_{27}R_{28}$, $-OOCR_{25}$, $-CR_{25}R_{26}OH$, and $-B$;

wherein $R_{25}, R_{26}, R_{27}, R_{28}$ and B are defined as in claim 13.

17. The method according to claim 11, wherein hTAS2R49 bitter taste receptor activity is determined by measuring a change in concentration of an intracellular messenger.

18. The method according to claim 17, wherein the intracellular messenger is selected from the group consisting of $Ca^{2+}$, $IP_3$, and cAMP.

19. The method, according to claim 11, wherein, in part (c), said variant has no more than 15 amino acid substitutions or deletions.

* * * * *

UNITED STATES PATENT AND TRADEMARK OFFICE
CERTIFICATE OF CORRECTION

PATENT NO.         : 8,709,745 B2
APPLICATION NO.    : 13/384956
DATED              : April 29, 2014
INVENTOR(S)        : Batram and Meyerhof It is certified that error appears in the above-identified patent and that said Letters Patent is hereby corrected as shown below:

In the Specification

Column 12,
Line 57, "thereof In" should read --thereof. In--

Column 12,
Line 61, "diphenidol HCI." should read --diphenidol·HCI.--

Column 17,
Line 4, "$NR_{11}R_{12}$;" should read -- -$NR_{11}R_{12}$--

Column 21,
Line 25-26, "$R_{25}R_{26}$" (does not begin new paragraph) should read --$R_{25}R_{26}$-- (begins new paragraph)

Column 24,
Line 30, "In preferred" (does not begin new paragraph) should read --In preferred-- (begins new paragraph)

Column 25,
Line 16, "It$_{27}$ is hydrogen" should read --$R_{27}$ is hydrogen--

Column 33,
Line 23-24, "or (N)" should read --or (IV)--

Column 34,
Line 15, "Preferably," (begins new paragraph) should read --Preferably,-- (does not begin new paragraph)

Signed and Sealed this
Twenty-first Day of October, 2014

Michelle K. Lee
*Deputy Director of the United States Patent and Trademark Office*

Column 34,
Line 54, "$C_{11}$, $C_{12}$," (begins new paragraph) should read --$C_{11}$, $C_{12}$,-- (does not begin new paragraph)

Column 35,
Line 45, "$C_7$, $^8$, $C_9$," should read --$C_7$, $C_8$, $C_9$,--

Column 40,
Line 17, "G-protein a" should read --G-protein α--

UNITED STATES PATENT AND TRADEMARK OFFICE
CERTIFICATE OF CORRECTION

PATENT NO.        : 8,709,745 B2                                        Page 1 of 1
APPLICATION NO.   : 13/384956
DATED             : April 29, 2014
INVENTOR(S)       : Batram et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 20 days.

Signed and Sealed this

Twenty-ninth Day of September, 2015

Michelle K. Lee
*Director of the United States Patent and Trademark Office*

SEQUENCE LISTING

<160> NUMBER OF SEQ ID NOS: 2

<210> SEQ ID NO 1
<211> LENGTH: 927
<212> TYPE: DNA
<213> ORGANISM: Homo sapiens

<400> SEQUENCE: 1

```
atgatgagtt ttctacacat tgttttttcc attctagtag tggttgcatt tattcttgga     60
aattttgcca atggctttat agcactgata aatttcattg cctgggtcaa gagacaaaag    120
atctcctcag ctgatcaaat tattgctgct ctggcagtct ccagagttgg tttgctctgg    180
gtaatattat tacattggta ttcaactgtg ttgaatccaa cttcatctaa tttagaagta    240
ataatttta tttctaatgc ctgggcagta accaatcatt tcagcatctg gcttgctact    300
agcctcagca tattttattt gctcaagatc gtcaatttct ccagacttat ttttcatcac    360
ttaaaaagga aggctaagag tgtagttctg gtgatagtgt tggggtcttt gttcttttg     420
gtttgtcacc ttgtgatgaa acacacgtat ataaatgtgt ggacagaaga atgtgaagga    480
aacgtaactt ggaagatcaa actgaggaat gcaatgcacc tttccaactt gactgtagcc    540
atgctagcaa acttgatacc attcactctg accctgatat cttttctgct gttaatctac    600
tctctgtgta acatctgaa gaagatgcag ctccatggca aaggatctca agatcccagc    660
accaagatcc acataaaagc tctgcaaact gtgacctcct tcctcatatt acttgccatt    720
tactttctgt gtctaatcat atcgttttgg aattttaaga tgcgaccaaa agaaattgtc    780
ttaatgcttt gccaagcttt tggaatcata tatccatcat ccactcatt cattctgatt    840
tgggggaaca agacgctaaa gcagaccttt ctttcagttt tgtggcaggt gacttgctgg    900
gcaaaggac agaaccagtc aactcca                                          927
```

<210> SEQ ID NO 2
<211> LENGTH: 309
<212> TYPE: PRT
<213> ORGANISM: Homo sapiens

<400> SEQUENCE: 2

```
Met Met Ser Phe Leu His Ile Val Phe Ser Ile Leu Val Val Ala
1               5                   10                  15

Phe Ile Leu Gly Asn Phe Ala Asn Gly Phe Ile Ala Leu Ile Asn Phe
                20                  25                  30

Ile Ala Trp Val Lys Arg Gln Lys Ile Ser Ser Ala Asp Gln Ile Ile
            35                  40                  45

Ala Ala Leu Ala Val Ser Arg Val Gly Leu Leu Trp Val Ile Leu Leu
        50                  55                  60

His Trp Tyr Ser Thr Val Leu Asn Pro Thr Ser Ser Asn Leu Glu Val
65                  70                  75                  80

Ile Ile Phe Ile Ser Asn Ala Trp Ala Val Thr Asn His Phe Ser Ile
                85                  90                  95

Trp Leu Ala Thr Ser Leu Ser Ile Phe Tyr Leu Leu Lys Ile Val Asn
                100                 105                 110
```

```
Phe Ser Arg Leu Ile Phe His His Leu Lys Arg Lys Ala Lys Ser Val
        115             120             125

Val Leu Val Ile Val Leu Gly Ser Leu Phe Phe Leu Val Cys His Leu
    130             135             140

Val Met Lys His Thr Tyr Ile Asn Val Trp Thr Glu Glu Cys Glu Gly
145             150              155                         160

Asn Val Thr Trp Lys Ile Lys Leu Arg Asn Ala Met His Leu Ser Asn
            165             170              175

Leu Thr Val Ala Met Leu Ala Asn Leu Ile Pro Phe Thr Leu Thr Leu
            180             185              190

Ile Ser Phe Leu Leu Leu Ile Tyr Ser Leu Cys Lys His Leu Lys Lys
        195             200             205

Met Gln Leu His Gly Lys Gly Ser Gln Asp Pro Ser Thr Lys Ile His
        210             215             220

Ile Lys Ala Leu Gln Thr Val Thr Ser Phe Leu Ile Leu Leu Ala Ile
225             230             235                         240

Tyr Phe Leu Cys Leu Ile Ile Ser Phe Trp Asn Phe Lys Met Arg Pro
            245             250             255

Lys Glu Ile Val Leu Met Leu Cys Gln Ala Phe Gly Ile Ile Tyr Pro
            260             265             270

Ser Phe His Ser Phe Ile Leu Ile Trp Gly Asn Lys Thr Leu Lys Gln
        275             280             285

Thr Phe Leu Ser Val Leu Trp Gln Val Thr Cys Trp Ala Lys Gly Gln
    290             295             300

Asn Gln Ser Thr Pro
305
```